US012079993B1

(12) United States Patent
Lochner et al.

(10) Patent No.: US 12,079,993 B1
(45) Date of Patent: Sep. 3, 2024

(54) COMPUTER EYE CARE SYSTEM

(71) Applicants: Scott J Lochner, Pasadena, CA (US);
Matthew E Lochner, Pasadena, CA (US)

(72) Inventors: Scott J Lochner, Pasadena, CA (US);
Matthew E Lochner, Cambridge, MA (US); George Edwards, Los Angeles, CA (US); Rebecca G Edwards Mayhew, Los Angeles, CA (US)

(*) Notice: Subject to any disclaimer, the term of this patent is extended or adjusted under 35 U.S.C. 154(b) by 900 days.

(21) Appl. No.: 17/088,411

(22) Filed: Nov. 3, 2020

Related U.S. Application Data

(60) Provisional application No. 62/936,158, filed on Nov. 15, 2019.

(51) Int. Cl.
G06T 7/00 (2017.01)
A61B 3/113 (2006.01)
A61B 3/12 (2006.01)
A61B 3/14 (2006.01)
A61B 5/00 (2006.01)
A61B 5/103 (2006.01)
A61B 5/117 (2016.01)
B64C 39/02 (2023.01)
G06F 18/22 (2023.01)
G06T 7/60 (2017.01)
(Continued)

(52) U.S. Cl.
CPC ........... G06T 7/0014 (2013.01); A61B 3/113 (2013.01); A61B 3/12 (2013.01); A61B 3/145 (2013.01); A61B 5/1032 (2013.01); A61B 5/117 (2013.01); A61B 5/681 (2013.01); A61B 5/7267 (2013.01); A61B 5/7275 (2013.01); B64C 39/024 (2013.01); G06F 18/22 (2023.01); G06T 7/60 (2013.01); G06T 7/90 (2017.01); G06V 40/193 (2022.01); G16H 10/60 (2018.01); G16H 40/67 (2018.01); G16H 50/20 (2018.01); G16H 50/30 (2018.01); G16H 50/70 (2018.01); B64U 2101/00 (2023.01); G06T 2207/20081 (2013.01); G06T 2207/30041 (2013.01)

(58) Field of Classification Search
CPC .......... G06T 7/0014; G06T 7/90; G06T 7/60; G06T 2207/20081; G06T 2207/30041; G16H 40/67; G16H 10/60; G16H 50/30; G16H 50/70; G16H 50/20; G06V 40/193; G06F 18/22; A61B 3/113; A61B 3/12; A61B 3/145; A61B 5/1032; A61B 5/117; A61B 5/681; A61B 5/7267; A61B 5/7275; B64C 39/024; B64U 2101/00
See application file for complete search history.

(56) References Cited

U.S. PATENT DOCUMENTS

2015/0362720 A1* 12/2015 Saito .................... G02B 25/001
359/644
2020/0258516 A1* 8/2020 Khaleghi ............. B60K 28/063
(Continued)

FOREIGN PATENT DOCUMENTS

VN          10033658 B   * 10/2022 ........... C07D 311/74

Primary Examiner — Khai M Nguyen
(74) Attorney, Agent, or Firm — Scott C Harris, Esq

(57) ABSTRACT

A system for remotely analyzing information, uses a computer, receiving eye data from a remote user. The computer processing the eye data to compare the eye data with information indicative of physical impairments. The computer uses the comparing to determine physical impairments in the user based on the eye data received remotely.

16 Claims, 4 Drawing Sheets

(51) Int. Cl.
*G06T 7/90* (2017.01)
*G06V 40/18* (2022.01)
*G16H 10/60* (2018.01)
*G16H 40/67* (2018.01)
*G16H 50/20* (2018.01)
*G16H 50/30* (2018.01)
*G16H 50/70* (2018.01)
*B64U 101/00* (2023.01)

(56) References Cited

U.S. PATENT DOCUMENTS

| | | | | |
|---|---|---|---|---|
| 2020/0372824 | A1* | 11/2020 | Hanson | B60W 40/08 |
| 2021/0097322 | A1* | 4/2021 | Mueller | A61B 6/504 |
| 2021/0169417 | A1* | 6/2021 | Burton | A61B 5/4857 |
| 2021/0378568 | A1* | 12/2021 | Coles | A61B 5/7267 |

* cited by examiner

COMPUTER EYE CARE SYSTEM

This application claims priority from provisional application No. 62/936,158, filed Nov. 15, 2019, the entire contents of which are herewith incorporated by reference.

BACKGROUND

The eye is a hollow organ about the size of a ping-pong ball, with an opening at the front that lets in light, and a gelatinous substance called vitreous filling most of the inside. It functions in a manner similar to a camera.

The aperture through which light enters the eye is the pupil, the black-seeming hole in the middle of the eye. The iris, the colored ring of muscle tissue surrounding the pupil, controls the amount of light coming in by narrowing or dilating the pupil. The "white" of the eye, or sclera, is a hard shield of tissue that encircles and protects the opening of the eye. A thin layer of tissue called the conjunctiva protects the sclera and connects the eye to the eyelid.

The eye's main focusing element is the cornea, a clear, hard tissue covering the iris and the pupil. The curve of the cornea bends, or refracts, light rays, focusing them on the retina at the back of the eye. A pool of fluid called aqueous humor fills a cavity between the cornea and the iris. Directly behind the iris is the lens, an elastic disc about the size and shape of an M&M candy, which flexes to fine-tune focus.

Lining the back of the eyeball is the retina, a complex, photosensitive membrane of many layers. This is the "film" of the eye and its most important part. When light is focused onto the retina, photosensitive cells translate the light into electrical impulses, which are then sent via the optic nerve to the brain, where an image is formed.

Current standard eye exams begin in the office of an optometrist or ophthalmologist with some questions and paperwork. You are typically asked to answer questions or fill out a form, providing information about your general health, any medicines you take, allergies or eye problems you have, and your family medical history. Asking these routine questions is necessary to establish background information that really does matter. Having high blood glucose or even taking a common, over-the-counter medicine can cause fluctuations in your vision that might make a difference in your exam.

Background complete, the next step in most eye exams involves assessing your visual acuity, or how well you can see. Vision is measured by the size of the letters you can easily read on the eye chart, which is usually about 20 feet away. If a person cannot read all the letters on the chart, it is because the shape of your eyeball, lens, or cornea causes light to focus either in front of or behind rather than right on the retina. Using a process called refraction, the eye doctor can find an eyeglass or contact lens prescription that bends the light correctly and enables you to see clearly.

Refraction can be done in several ways. The doctor or a technician may hold up various lenses and ask questions about which combination helps you see best. She may shine a special light into your eyes to measure its shape (a process called retinoscopy), or she may use any one of several instruments that do automated retinoscopy. Each eye is tested separately, then both are tested together. In routine eye exams, if you already wear glasses, your current glasses prescription is read in a machine called a lensometer. The strength of the present prescription is then compared to the best possible correction, determined by refraction.

Refraction is routinely performed not necessarily to prescribe new glasses but to determine how well the person can see with the best possible lenses. If a person does not have normal visual acuity even with the optimal correction, it could be a sign of a more serious problem. (In nonroutine eye exams, such as those done by a retinal specialist, refraction is rarely done.)

A person's vision normally means his central vision, or what he can see looking straight ahead. Everything a person can see up, down, and sideways while looking straight ahead is called peripheral vision. Peripheral vision is measured and recorded as a "visual field." Measuring the visual field is often part of a routine eye exam. The test can be as simple as noting how far out to the side you can see the doctor's wiggling pencil while looking straight ahead, or it can be more sophisticated.

In prior times, doctors tested visual field by having a person look at a black felt screen with one eye at a time, while they moved a small circle on a stick from the edge toward the middle of the screen until the person could see it. Sticking a pin in the felt at that spot, they repeated the test from different angles, finally drawing the pattern of pins on a sheet of paper. That method gave reliable information, but it was time-consuming. Now there are automated perimeters that can give an accurate measure of a visual field in about three minutes. Looking into the automated perimeter, you signal when you see flashes of light. The computer maps your field of vision based on which flashes you see and which you miss.

The next part of a routine eye exam is an external exam, which is a visual inspection of the parts of the eyes that can be seen with just a flashlight. An external exam can be performed quickly. The eye doctor observes the condition of the eyelashes; the position, motions, and skin condition of the eyelids; the actions of the eye muscles (assessed by watching the movements of the eyes); the appearance of the whites of the eyes and the conjunctiva; and the size of the pupils and their reactions, particularly to light.

To see the internal structures of your eyes, the doctor will next ask you to rest your chin on a chinrest and press your forehead against a strap, while she aims an instrument at you called a slit lamp. The slit lamp is both a high-powered microscope and a light source that is focused to form a flat sheet. Because the front parts of the eye are transparent, the sheet of light can show a cross section of the front structures of the eye, the way a sunbeam shining across a room can show the dust in the air. Depending on the width of the light beam and the lens, the slit lamp can give a magnified, three-dimensional view of the cornea, the iris, or the lens, or it can show a cross section from front to back of the eye, through the cornea, aqueous humor, lens, and vitreous. With an additional lens (either a handheld lens or one that fits directly against the cornea), the doctor can see all the way to the retina, blood vessels, and optic nerve at the back of the eye.

Another instrument used to view the interior of the eye and the retina is the ophthalmoscope. The most familiar type of ophthalmoscope is the handheld direct ophthalmoscope, which looks like a flashlight. Doctors use it to see the central retina. They may also use an indirect ophthalmoscope, which is a head-mounted instrument like a coal-miner's lamp that shines into the eye and condenses the out-coming light into a three-dimensional image of the retina. Looking through the lens of the instrument and a handheld lens held in front of the patient's eye, the doctor sees a wide, panoramic view of the retina.

To obtain the best view with the indirect ophthalmoscope—and sometimes with the slit-lamp—the doctor will first dilate your pupils with eyedrops, a procedure that may be unpleasant but not painful. Because your pupils may still be dilated for some time, it is a good idea to bring a pair of sunglasses and make arrangements for transportation after the exam.

To the person having the eye exam, the standard tests may just seem like a barrage of bright lights. But to the eye doctor, they provide invaluable information.

Current State of Teleophthalmology in The United States.

Telemedicine is "the use of electronic information and communications technologies to provide and support health care when distance separates the participants."

The use of telemedicine in ophthalmology is currently in its infancy and has yet to gain wide acceptance. Current models of telemedicine in ophthalmology are largely performed via "store and forward" methods, but some remote monitoring and interactive modalities exist.

Hospital Evaluations/Emergency-Based Evaluations.

Teleophthalmology in the emergency department (ED) setting has the opportunity to provide rapid specialty support to frontline providers. ED needs are unique compared with other areas of telemedicine because needs are typically immediate, requiring real-time teleophthalmology, and often have an interactive audio or video component.

Annually, approximately 2 million people seek ophthalmic care in the ED setting in the United States. Approximately 33% of these patient encounters occur in nonmetropolitan settings. More than 50% of EDs do not have available eye care professionals. Furthermore, data indicate that house officers are uncomfortable dealing with eye emergencies despite increasing availability of equipment, possibly leading to further disparities in care. This could be further aggravated when nonphysician providers evaluate patients in the urgent care setting without physician staffing. Specialty input at the front lines of patient care traditionally has been filled by onsite eye care professionals or by transporting patients to the eye care professional.

In the United States, there are few applications of teleophthalmology in the emergency setting. The US Army used a teleophthalmology tool for consultations in military settings abroad. As of the end of 2017, however, live audio/video services were not available, and communication occurred over e-mail, with 87% of consults accompanied by photographs.

As of the end of 2017, it appears the only known emergency teleophthalmology program deployed in the United States was at the University of Pittsburgh. Emergency department physicians were given an iPhone 4S (Apple, Cupertino, CA) and an ophthalmoscope adaptor to capture images. Remote ophthalmologists used the clinical history, basic examination findings, and images provided by emergency staff to triage patients. A review of 50 consecutive patients demonstrated that off-site ophthalmologists can make "accurate and safe triage decisions" with this solution.

Teleophthalmology in the emergency setting has the potential to expand the care team, promote patient-centered care, and improve care coordination.

Barriers to Teleophalmology. Although telecommunication barriers such as bandwidth and storage limitations have largely been overcome in the United States, the cost of ophthalmic imaging equipment and other hardware can be prohibitive (although costs are falling).

Also, teleophthalmology in the outpatient setting relies on already overburdened primary care clinics to perform additional tasks and ensure patient compliance with recommendations from the telemedicine evaluation.

A unique barrier to deployment of telemedicine in ophthalmology is physician perspectives. 59% of ophthalmologists reported "low confidence" in their ability to make decisions based on images alone. This contrasts to the University of Pittsburgh's experience with emergency teleophthalmology, where all patients in their series who required urgent ophthalmic care were appropriately triaged for evaluation. Medical liability also is quoted as a reason for pause; however, medical images are potentially protective because they allow objective documentation of examination findings, mitigating medical malpractice concerns.

Successful application of teleophthalmology in any of its forms requires development of image acquisition, transfer, and storage systems that adhere to patient confidentiality standards, identification and mitigation of professional liability risk, clear reimbursement/payment streams, and consistent and continual training of involved personnel.

Ophthalmic telemedicine in the United States is in its infancy but has the potential to improve access to care, decrease cost of care, improve adherence to evidence-based protocols, and improve outcomes.

(https://www.ncbi.nlm.nih.gov/pmc/articles/PMC6020848/)

The technological advancement of wireless communication devices is a major development in telehealth. This allows patients to self-monitor their health conditions and to not rely as much on health care professionals. Furthermore, patients are more willing to stay on their treatment plans as they are more invested and included in the process as the decision-making is shared. (https://en.wikipedia.org/wiki/Telehealth)

SUMMARY OF THE INVENTION

The present application describes an eye care system which is carried out using one or more computers.

It is an object of the present invention to use a computer to carry out eye care for humans and/or animals through use of a portable or mobile wireless computer system, together with peripherals that work with other parts of the invention.

The invention is intended to assist with eye care of humans and/or animals, and also to assist with other health care issues of humans and/or animals that may be indicated and potentially identified through the examination of eyes and eye movement ("eye data"). The term "eye data" as used herein means any data that characterizes any parts of the eye. Some examples of eye data are referred to here, but this term includes all data about all parts of the eye, and is not limited to those enumerated data or parts. This is intended to make the eye care better, faster, and cheaper.

This is based on the inventor's recognition that monitoring and examining changes in eye health can be useful in alerting one to and potentially protecting one from many health issues and problems. The evaluation of eyes, parts of eyes (including eyelids eyelashes, eyebrows, skin under the bottom of the eyelid, eye gaze), and eye movements and blinking(eye data) can assist in the identification and treatment of the health of eyes per se, and can also assist in the potential identification of other related health issues. It is well-known, for example, that more than half of the brain's function is involved with vision. Consequently, many eye disorders and vision loss can be associated with problems in the optic nerve or brain, not the eyes themselves. Any data of this type is included as part of eye data.

The evaluation of eye data can help to potentially indicate, for example, if the human and/or animal has had a concussion, has other brain trauma, and/or their general neurological condition. This can be useful for such health care professionals as ambulance personnel, neurologists and anesthesiologists.

Further, the color and state (static and/or dynamic) of various portions of eyes can potentially indicate, for example, high blood pressure, a clotting disorder, liver diseases such as jaundice, hepatitis, and cirrhosis, nervous system disorders, high cholesterol and triglycerides, increased heart attack and stroke risk, and more, as will be more fully discussed herein.

The inventor believes that the collection of eye data in a similar way whereby the collection and analysis of the data, including a comparison of your eye data trends over time, can reveal a number of significant "indications" that may play a role in your general health.

Also, it is the intention of the invention, through its use of "machine learning" and "deep learning" software, to uncover new correlations between and among eye data and general health. The invention describes correlating, in one embodiment using "deep learning" software to do so, the data results from the blood data and the eye data, to find new discoveries from such comparisons.

The following comprises some additional potential types of "health data" of humans and/or animals that can optionally be obtained from a Subject (or the Subject's medical Professional) that can be compared and cross-referenced (by the invention) with eye data of the Subject (as collected and analyzed by the invention), in real time, near-real time, or distant time, so the compared cross-referenced eye data and "health data" information, if statistically relevant, benefits science and humanity in terms of new discoveries and improvements, but also potentially directly benefits the Subject (or the Subject's owner if the Subject is an animal) by providing a "firmer indication"/more definitive indication/stronger indication of a Subject's Condition and/or the trend and speed of the trend in a Subject's Condition (than might otherwise be the case with only the Subject's eye data alone).

In one embodiment, this is referred to as "eye data-plus", for a more holistic view of the indication of a Subject's Condition and/or trend and speed of the trend of a Subject's Condition.

The Invention can Compare and Cross-Reference Eye Data and "Health Data" as described in this patent application and as described in the following. The invention to effectuate the comparison and cross-referencing of:
(x) Subject eye data (as obtained and processed by the invention) with
(y) additional potential types of Subject "health data" (i.e., e.g., but without limitation, blood, Body Mass Index, blood pressure, pulse oximetry, weight, et al., all with the date and means acquired, etc.).

This data comparison and cross-referencing (which may involve numerous combinations and/or permutations of the same) can be done, without limitation, through the use of specialized "if-then" and/or AI software known to those skilled in the art, as well as through the use of other methodologies known to those skilled in the art.

Embodiments can be used to simplify, make more convenient, and make more objective (and therefore better) the identification of potential health issues with regard to not only eyes per se, but also other health issues that may be indicated through an examination of eye data.

The invention is also intended to enable the remote, at-a-distance, examination and evaluation of eye data, in real time, near real-time, or delayed time, by health care professionals ("Professionals").

In addition, the embodiments describe, through monitoring eyes and eye movements, the invention's ability to:
(i) measure eye movement, et al. to assist in better and more safely measuring the administration and use of general anesthesia on a Subject to whom or which the anesthesia is being applied.
(ii) act as an alternative means of protecting a Subject from corneal abrasions during general anesthesia, typically caused by direct trauma, exposure keratopathy/keratosis, or chemical injury.
(iii) ameliorate during general anesthesia the reduction in a Subject's tear production and tear-film stability, which if unameliorated may result in corneal epithelial drying and reduced lysosomal protection.
(iv) assist in being an additional and better and safer tool to measure a Subject patient's emergence from general anesthesia (the immediate time after the general anesthesia or sedation), which requires careful monitoring because there is still a risk of complication.

Further, the embodiments describe, through monitoring eyes and eye movements, to assist in:
(i) the measurement of human veracity/truth-telling.
(ii) the measurement of the eye or difficulty with which human and/or animal subjects are able to perform certain tasks, such as, and without limitation, test problems or operating a new machine or device.
(iii) the measurement of human and/or animal preferences (such as, and including without limitation, for example, visual, auditory, and haptic/touch preferences).

In other embodiments, the invention is intended to identify unique biometric markers in the eyes, parts of eyes, or eye movements of users that may be used in a variety of ways as described herein. The use may be in opening or locking locks, automatic door opening or closing, computer logins, security identification, identification for accidents or surgery, or other applications.

Also, the evaluation of the eyes of a deceased human and/or animal can reveal important information such as approximate time of death, and other useful information further described herein.

DETAILED DESCRIPTION

Figure 1:
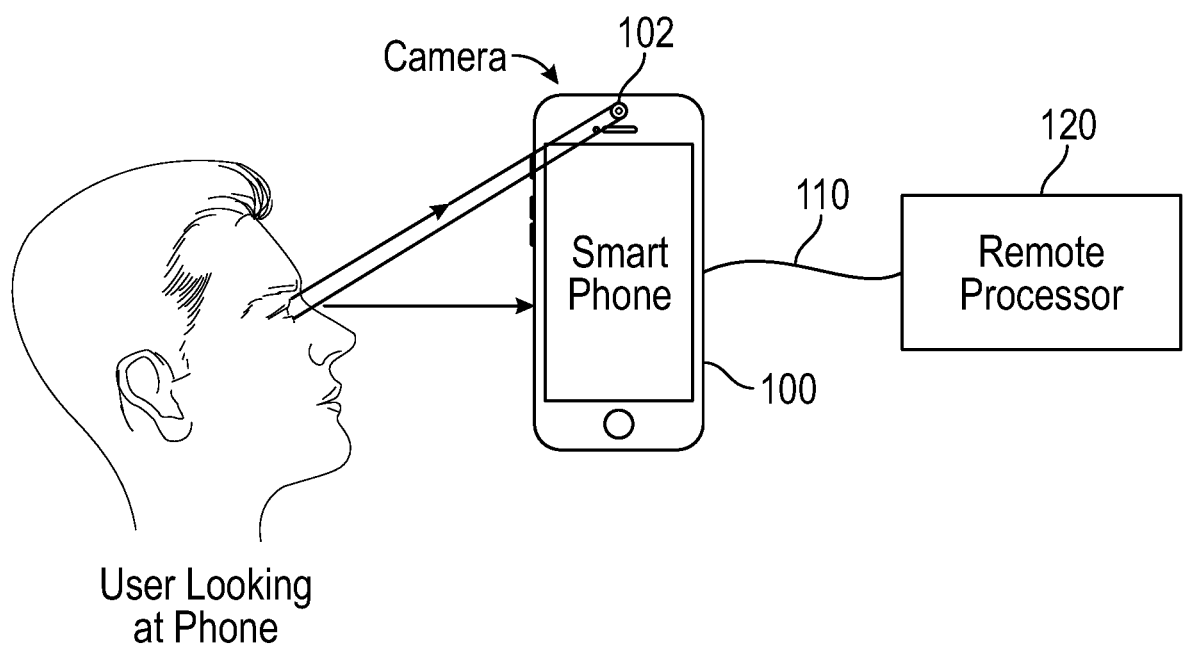
FIG. 1 illustrates an app being used to obtain eye data.

An embodiment describes remotely characterizing and determining issues with patient health based on eye examinations.
1. Replicating Much of the Traditional In-Office Exam At-a-Distance.
   a. Initial Set-Up. Similar to current eye exams, the invention envisions the person whose eyes will be examined initially answering written or verbal questions online (by a Professional or AI-powered chatbot), or by verbally responding or filling out a form online, providing information about his or her age, gender, ethnicity, general health, any medications being taken, any allergies or eye problems, a brief medical ocular and surgical history, and family medical history. However, instead of this taking place in your optometrist's or ophthalmologist's office, this process begins in Subject's home (or, for example, in a local pharmacy office or school).

Depending on the setting, additional information may be collected such as Body Mass Index, blood pressure, pulse oximetry, smoking status, and dietary habits.

b. Advantages. For the person whose eyes will be examined or monitored, the Subject saves time and expense in not having to schedule a formal appointment with an optometrist or ophthalmologist, and not having to travel to-and-from that Professional's office once, if not a number of times. Further, in this age of epidemics and contagious infections, there is the benefit to Subject and Professional alike that no human contact or close proximity is necessary.

2. Teleophthalmology: Version 1—Being Virtually Side-by-Side with a Human Professional. Useful for Professionals practicing teleophthalmology, and known to those skilled in the art, is the use of:

a. Visual acuity tests (typically using a standard Snell chart).

b. Automated refractors (key in measuring the eye's refraction state in sphere, cylinder, and axis, measuring the estimated correction needed for the Subject's eyes to focus properly at a distance).

c. Non-contact tonometry (as in air-puff tonometry, used to measure intraocular pressure in a non-invasive manner, screening for eye diseases such as glaucoma).

d. Fundus photography (including without limitation using fundus autofluorescence) digital non-mydriatic retinal cameras (which allow for the imaging of the retina, retinal vasculature, optic disc, and macula, important in assessing diseases such as diabetic retinopathy, age-related macular degeneration, glaucoma, and hypertensive retinopathy, and also potentially for cataracts).

e. Optical Coherence Tomography (OCT) (a non-invasive imaging test that captures high resolution, cross-sectional images of the retina, retinal nerve fiber layer, optic nerve head, and angular segment, which assists in assessing age-related macular degeneration, glaucoma, and diabetic retinopathy, as well as the risk for glaucoma).

f. Thermal Camera Imagery (also known as thermography, which uses infrared thermal imaging cameras, and is recognized as a valuable diagnostic method in ophthalmology).

3. Teleophthalmology: Version 2—Using "Machine Vision" Together with Rules-Based Programs, Machine Learning and AI Software (including various "flavors" of deep learning software) to Provide Indications and Predictions.

a. Initial Set-Up. The initial set-up is virtually the same as in B.(1)(a) above.

b. Advantages. The invention can perform the periodic eyes review and examine the eyes of a Subject much more quickly and comprehensively than a human eye expert can, because as a computer-based system:

(i) it has better and faster access to computer database records (if any) of prior eye examinations of the same Subject;

(ii) it can perform an objective eye comparison of one eye to the other eye during the same time period (i.e., e.g., pattern and color comparisons, etc., using computer vision and other relevant software), and provide objective measurements, while a human's measurements are typically subjective (and vary from human to human);

(iii) it can perform eye comparisons (i.e., e.g., pattern and color comparisons, etc., using computer vision and other relevant software), comparing a new digital picture/image or digital video clip to a prior digital picture/image or digital video clip (if any) of the eyes of the same Subject, revealing eye condition changes over relevant time periods;

(iv) it can perform eyes comparisons (i.e., e.g., pattern and color comparisons, etc., using computer vision and other relevant software) comparing new digital picture/image or digital video clips of the Subject to computer database records of digital picture/image or digital video clips of "healthy" eyes or eyes with known condition(s) displayed in eyes that are similar to the potential condition(s) of the Subject displayed in eyes;

(v) it does not require the time expenditure of travel by the Subject to the offices of a human eye expert, or of the human eye expert to the location of the Subject;

(vi) AI systems, unconstrained by prevailing theories and biases, can identify new targets by spotting differences at the level of tissues in healthy eyes, and differences that might elude or mystify a human scientist.

(vii) if programmed correctly, software does not consciously or unconsciously positively or negatively discriminate against the Subject whose eyes are being examined. It is not sensitive to age, gender, ethnicity, race, et al.

(viii) any benefits of the invention not described herein.

c. Follow-up Questions and Follow-up Data Collection. Somewhat similar to the manner in which certain artificial intelligence deep learning programs use back-propagation to improve the efficacy of the predictiveness of the program, the invention may ask follow-up questions of the Subject to obtain data to refine and improve the Rules-Based Program/"if-then" and/or predictive aspect of what the invention is measuring. The invention may also suggest to the Subject that Other Information be obtained and provided.

Much of the information in the present specification comes from the inventor's recognition that technology for obtaining image information is continually improving. For example, the camera and camera-related software on smartphones and pads, using artificial intelligence (including deep learning) in the smartphone or pad (and in the cloud to which the pictures and video are sent)—will continue to improve and do amazing things. This will only get more ubiquitous with the coming of new mobile technologies such as 5G, and the continual evolution of Internet of Things (IOT). In addition, natural language processing and AI-powered chatbots will continue to improve.

Use of the "elastic cloud" and the computing and storage therein, and the amazing cost-effective things that can be accomplished on that platform, and the migration thereto has only just begun.

The user-end portion of the invention (the end closest to the eye(s) of the human and/or animal being evaluated), is shown in the Figures. A first embodiment uses 1. Smartphone (or Similar Device) (the "Device"
   a. A smartphone 100 or similar device (the "Device"), together with a software application loaded in the Device, used by a user who previously provides relevant personal information regarding the user's age, health, and other personal details independently or through the Device, and sets certain parameters provided in the software application.

The camera 102 of the Device 100 operates to automatically turn on and video record eye data at pre-selected intervals and for preset durations. The eye data can be color data including data about the user's eyes, eye parts, and eye movement. The pre-selected intervals can be, for example, every day, every week, every month. The preset durations can be 10 seconds, 30 seconds, or 2 minutes. In one embodiment, this is automatically done while the user is looking at the display screen of the smart phone 100, doing whatever screen time activities the user happens to be doing.

The information from the obtained video is transmitted at 110 to a remote processor, for example a cloud processor. The user can give prior consent to obtaining and processing this information as described herein.

The Subject/user can speak by a Device built-in microphone or separate wired or wireless microphone), and Subject/user can hear by a Device built-in speaker or separate wired or wireless earphones or headphones. The Subject/user can hear a Professional and/or an AI-powered chatbot.

Various different types of add-on cameras (which are part of the invention) can be added to the Device as desired to allow capture of eye data from various parts of the eyes of the Subject. Alternatively, a Device can be a stand-alone device with just the appropriate type of camera (i.e., it would not be an "add-on" camera to a smartphone-type device)

In a first embodiment, the remote processor 120 comprises sending the information to a Professional, e.g., one selected by the user, who receives the eye data and reviews and examines the video in real time (potentially also interacting with the user by audio or otherwise in real time), near-real time, or delayed time. The eye data can be evaluated, displayed, and potentially manipulated in various ways, including, without limitation, (a) being enlarged/magnified, (b) replayed in slow motion, (c) displayed in augmented reality and/or virtual reality three-dimensionality, (d) displayed with alternative coloration for better contrast, or (e) compared with other eye data either directly by the Professional or through the use of artificial intelligence software, and report back to the user.

In another embodiment, the remote processor 120 comprises the data being compared by a software program to other stored eye data about the user. The processing comprises the software processing the data to find a change in some portion of the user's eye data. The program can also compare the eye data and its changes to other patterns and eye data changes in its memory. Examples of the kinds of things that it looks for include comparing the eye data with data indicative of healthy eyes and/or eye movements. The eye data can also be compared with eyes and/or eye movements of others who have specified physical impairments. By finding similar eye data to those who have specified physical impairments, this can postulate similar kinds of physical impairments in the user whose eye data is being analyzed. This system can report back information to either (a) the user, or (b) a Professional.

Another embodiment adds this to a deep learning software program which forms part of the remote processor 120. The deep learning program evaluates what it receives based on what it has previously learned about the eye data and related general health information of the particular user, and reports its findings and indications back to either the user, or a Professional pre-selected by the user.

The Device software application program may be set for a Professional to be able to examine the user's eyes and/or eye movements remotely, at a distance, in real-time while interacting directly with the user by audio or otherwise. Related thereto, the Device software application may be set whereby the Professional can take control of the Device and its software application remotely in order to better conduct the examination of the eyes and/or eye movements of the user.

Another embodiment may use an augmented reality scanner (a software application addition), or a 3D camera attachment to obtain 3D information about the eyes. This can allow the user's eyes and/or eye movements to be transmitted, remotely viewed at-a-distance and examined (i.e., a "live" viewing) and/or recorded, transmitted and remotely viewed and examined, by a human or software, with a certain amount of three dimensionality and the ability for potentially greater manipulation of the video display or video recording on the receiving end, by either a Professional or by artificial intelligence software.

Another embodiment uses a laser-powered 3D camera (rumored for inclusion in one or more of the versions of iPhone 12), and/or a LiDAR scanner (a form of which is currently found in the iPAD Pro 2020, and which is rumored for inclusion in one or more of the versions of iPhone 12, which LiDAR scanner can accurately judge distances and therefore depth, and allows for improved augmented reality.

d. An advantage of the software application as used in a Device is that it can automatically turn on the video camera of the Device at preset intervals. Also, other than initially configuring the software application, the user does not need to think or remember anything: the software application performs its function and monitors the user's eyes and/or eye movements and reports its findings and indications back, either directly to the user or through a Professional pre-selected by the user as to whether there is any potential issue the software application in the cloud or Professional pre-selected by the user identifies on which the user might want to follow-up.
   e. The user may want this eyes report and backup to be forwarded to the user's insurance company or to any other party, which can be a pre-selected function of the software application program.

Figure 2:
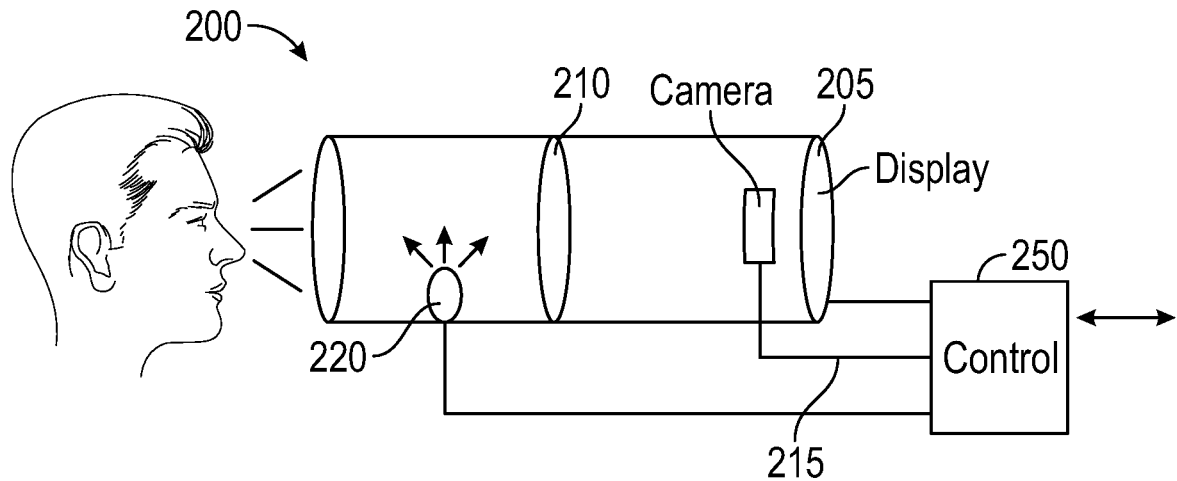
FIG. 2 shows a periscope embodiment.

A second embodiment uses:

2. A Chamber-Plus-Device.
   a. Another embodiment describes a device 200, shown in FIG. 2, in one configuration similar to a periscope, with a chamber which on one end 200 the user peers into (with or without glasses, with one eye or both eyes), and on the other end the Device is attached with its video screen 205 display facing inward (the "Chamber-Plus-Device"). The Chamber, in the configuration similar to a periscope, has internal magnifying mirrors 210 tilted at correct angles so that the Chamber enlarges the user's eyes so the attached Device's camera is better able to capture the static and dynamic image of a larger eye or eyes, eye parts, and eyelid, etc., and so that the user can clearly see the attached Device's display-screen.

Alternative 1: The Chamber configuration can be a straight tube, and the user peers through non-distorting magnifying lens(es) facing the inward facing attached Devise camera on the other end of the tube.

Alternative 2: Adding a macro lens on the attached Device camera to better capture the image of a much larger eye or eyes, eye parts, and eyelid, etc. than would otherwise be the case.

b. Using the Chamber-Plus-Device is similar to using the Device alone, except:

i. The Chamber offers precise control of the amount of light in the Chamber so one can compare "apples-to-apples" light-wise as opposed to having the software application alone controlling light conditions in various less controlled settings (i.e., which settings vary depending upon where and when the video of the eyes is recorded: for example in a dark room, in sunlight, or at dusk), unless otherwise "equalized" by the invention. Note: Physicians who use a penlight for certain eye tests, which is common today, are being subjective, whereas the invention seeks to create objectivity and superior health care as a result by equalizing the light from test to test.

ii. The Chamber's internal mirrors or non-distorting magnifying lens(es) 210, enlarge the user's eyes so the Device camera 215 is able to better capture the static and dynamic images of a larger eye and eyelid, etc. Alternative: Adding a macro lens on the Device camera to better capture the image of a much larger eye and eyelid than would otherwise be the case.

iii. The Chamber offers a fixed distance (i.e., focal range) between the eyes of the user and the Device camera, which can provide clearer and more consistent video of the eyes and eye movements of the user. Note: The Chamber may allow for an adjustment in the fixed distance (i.e., focal range) between the eyes of the user and the Device camera.

iv. The Chamber offers greater stability control for the user whose eyes and/or eye movements are being examined as opposed to having the software application alone controlling "jitter" stability.

v. The Chamber allows for the introduction of actual lights 220 into the Chamber itself, which can be used in various ways (e.g., brighter, dimmer, strobe, left-to-right, different color and types of lights, etc.) for the examination of the user's eyes, beyond just the lighting coming from the Device itself (including light not just the brightness of light from the Device display screen, which can be adjusted, but also light from a Device light and/or flash). For example, without limitation, pupil reflexes can be tested using three traditional procedures: (i) the light response pupil test, the swinging flashlight pupil test, and the near response pupil test. This can be done using the Chamber for the lighting instead of using the Device for the lighting.

vi. The actual lights in the Chamber can be controlled remotely by a Professional, or by the software application program running on controller 250. The controller itself can be wireless or wired connection between the Device and the Chamber to effectuate such Chamber lighting control remotely.

vii. The Chamber allows for additions to it, such as the ability to send a puff of air into the user's eyes to remotely test for glaucoma.

viii. Unlike with the Device and application software alone, in general the Chamber-Plus-Device must be used consciously by the user, since the user generally must consciously put his or her eyes against the one end of the Chamber, and accordingly in general the Chamber-Plus-Device cannot be set on automatic as is possible with the Device and application software alone. That said, the Chamber-Plus-Device can be set on semi-automatic for many test functions. These semi-automatic functions can be initiated by conversations between Subjects and Professionals and/or invention AI-powered chatbots or by other means. Notwithstanding the foregoing, third party professionals, such as ambulance attendants, neurologists and anesthesiologists, can use the Chamber-Plus-Device to record the eyes and eye movements of a conscious or unconscious "user" and configure the application software to record the "user's" eyes and eye movements at automatic periodic intervals.

ix. The Chamber itself can be designed in many configurations, one better than the other depending on the intended user (e.g., the owner holding it up to the eyes of a dog or a cow).

Figure 3:
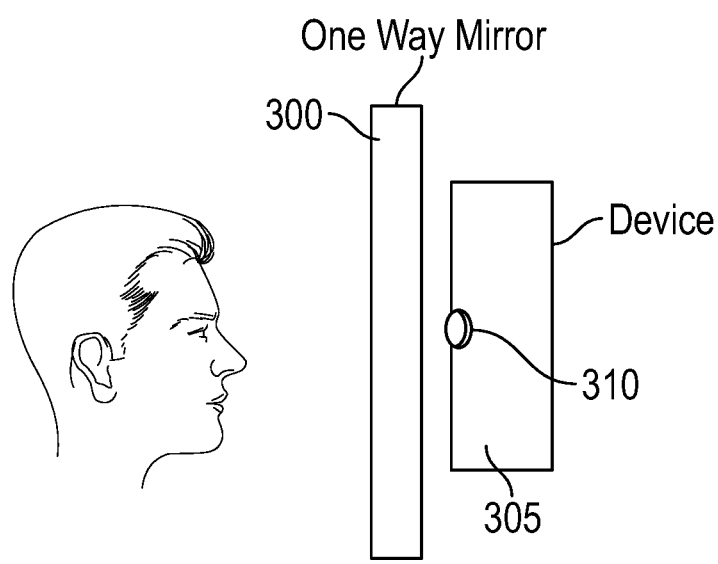
FIG. 3 shows a one way mirror embodiment.

3. The "Magic Mirror". A "magic mirror" 300, shown in FIG. 3, is a one-way mirror (which may be made of different substances) in which behind the one-way mirror on the non-reflective side there is the Device 305, with its camera 310 facing toward the non-reflective side of the mirror so it can view and record the eyes of the user who is on the reflective side of the mirror ("Magic Mirror"). By its nature, the user cannot see the Device 305, since it is on the other side of the Magic Mirror.

a. The Magic Mirror is an implementation essentially exactly like item 1(a) above (i.e., the Device by itself together with a software application), except that the Device with a software application resides behind the Magic Mirror (which can be portable or stationary), and instead of looking directly at the Device display screen and having the user's eyes automatically recorded while the user is doing whatever activity, with the Magic Mirror the user looks at the Magic Mirror to comb his or her hair, brush his or her teeth, or to apply his or her make-up, and during that time the camera behind the Magic Mirror automatically turns on and video records in color solely the user's eyes, in detail, and transmits the video to "a cloud", etc.

The Magic Mirror can have a built-in microphone (e.g. built-in) voice input for the Subject and built-in speaker (e.g. built-in) audio output for a Magic Mirror. In an alternative embodiment, the microphone and speaker can be external and attachable. In any event, Magic Mirror should have optional AI-powered chatbot (audio input and output) capability. If selected, the invention's AI-powered chatbots can assist in providing audio input and audio data output for the benefit of the Subject. For the Subject, for example but without limitation, the invention chatbot can ask questions, make commands, or attempt to inform the Subject of specified information. All of these audio outputs are programable and optional. Human Professionals could substitute for the invention chatbot.

Another name for a Magic Mirror is a glass teleprompter mirror, also known as a "beam-splitter mirror" or a transparent mirror. It is a semi-transparent mirror that reflects text while allowing flawless recording through it, in 1080p, 4K, and higher resolutions. The back side of the mirror has an anti-reflective coating which prevents "ghosting", which is a double image you would see when using standard glass.

There are various types of beamsplitters. Standard beamsplitters, which split incident light by a specified ratio into two (or sometimes more) beams, which may or may not have the same optical power, that is independent of wavelength or polarization state, are ideal for one-way mirrors.

4. Another embodiment uses a Wearable/Digital-Computer Watch (or Similar Device) such as the Apple Watch but with Camera(s) In/On/Connected To It (the "Watch").

Camera(s) can monitor the wearer's eyes when the Watch-wearer looks at the Watch. The Watch can (i) locally process eye data and have a transceiver of its own to transmit eye data to the cloud, and in turn receive data from the cloud, or (ii) by Bluetooth or other wireless means can connect to a smartphone or other similar device to process and transmit data to the cloud, and in turn receive data from the cloud and transmit it to the Watch.

The Watch can have one camera, multiple cameras, and/or various types of cameras on it. Two cameras, for example, can capture eye images in 3D, and if the Watch-wearer has a specific medical condition that the Watch-wearer wants to monitor through the wearer's eyes (including a condition or potential condition of the eyes caused at least in part by the body or brain disease or condition), the Watch-wearer can get a Watch with a Watch camera or cameras in it that can examine that area of the eye necessary to monitor that condition. Also, the Watch can monitor the eyes for a condition that has been "treated", to assist in determining how the treatment is working and progressing.

In one embodiment, the Watch may have a laser-powered 3D camera (rumored for inclusion in one or more of the versions of iPhone 12), and/or a LiDAR scanner (a form of which is currently found in the iPAD Pro 2020, and which is rumored for inclusion in one or more of the versions of iPhone 12), which LiDAR scanner can accurately judge distances and therefore depth, and allows for improved augmented reality.

The invention can report the results of the eye examination and monitoring back to the Watch-wearer (i) on the Watch, (ii) on the connected smartphone or other similar device, (iii) to the Watch-wearer's selected health professional, and/or (iv) to the Watch-wearer's selected health insurer.

The Watch can also be used for all other aspects of the invention that might involve a conscious human Watch-wearer as described in this patent application.

The Watch has (i) built-in microphone or separate wired or wireless microphone; and (ii) a built-in output speaker and/or separate wired or wireless earphones or headphones, so the Subject/user has the ability to hear and speak through the Watch.

The Watch may also have an AI-powered chatbot (audio input and output) capability. The invention's AI-powered chatbots can assist in providing audio input and audio data output for the benefit of the Subject. For the Subject, for example but without limitation, the invention chatbot can ask questions, make commands, or attempt to inform the Subject of specified information. All of these audio outputs are programable and optional. Human Professionals could substitute for the invention chatbot.

In an embodiment, are two versions of the Watch: (i) a standalone Watch, in which all the functionality resides in the Watch, and (ii) a Watch that works wirelessly together with the Device or a smartphone, in which some of the technology is in the Watch, and some in the Device, and they work together, with the Watch piggybacking off the Device's transceiver and battery, et al. (in a manner similar to how the first generation Apple Watch functioned).

5. Amazon Echo Show (or Similar-type Device) Which Either Has Its Own Transceiver or Wirelessly or By Wire Interacts with a Smartphone (or Similar Devise)

One modality of the invention is something somewhat similar to the Amazon Echo-Show (which connects to the Amazon cloud and allows for 2-way video and audio conference calls when coupled by Bluetooth with, for example, an iPhone or similar device), which, like the iPhone, can have various different types of add-on cameras (which are part of the invention) attached to it, to allow it, as desired by the Subject or a Professional, to capture eye data from various parts of the eyes of the Subject.

Alternatively, it could be a standalone device with just the appropriate type of camera (i.e., it would not be an "add-on" camera to the Amazon Echo Show-type device). This may use some components of an attached phone in order to carry out the communication.

The Amazon Echo Show-type device would either have its own transceiver or piggy-back off the transceiver of a smartphone (or similar type device) similar to what the Amazon Echo-Show currently does.

A basic Amazon Echo Show-type device might have only one or two different types of cameras, and the specialized device might have many different cameras (activated as determined by the Subject or Professional and/or determinations made by the invention software [which may want greater magnification, a different filter, a different camera, et al.]).

Another embodiment uses "Chamber-Plus Amazon Echo Show-Type Device", as a variation, with similar benefits as described in the Chamber-Plus-Device section above.

6. Special Input Eyeglasses with Cameras Looking Inward at Eyes of the Subject/Wearer ("Special Input Eyeglasses").

The Special Input Eyeglasses have cameras looking inward at the eyes of the Subject/wearer.

There are three types of Special Input Eyeglasses:

(i) Those that are wirelessly connected to a smartphone or its equivalent (similar to the first generation Apple Watch as an example of similar functionality), in which the Special Input Eyeglasses themselves would lack internet connectivity and most if not all of the data is processed in the smartphone or its equivalent. These Special Input Eyeglasses would run on batteries that could be charged wirelessly, but optionally could be connected to a power main.

(ii) Those that can function as a purely standalone device, with no need for a smartphone or its equivalent for functionality. These Special Input Eyeglasses could run on batteries that could be charged wirelessly or could be connected to a power main.

(iii) Those that are tethered to a PC or non-smartphone (i.e., more powerful) computer for functionality. These Special Input Eyeglasses could run on batteries that could be charged wirelessly, or could be connected to a power main.

The Special Input Eyeglasses may have a laser-powered 3D camera (rumored for inclusion in one or more of the versions of iPhone 12), and/or a LiDAR scanner (a form of which is currently found in the iPAD Pro 2020, and which is rumored for inclusion in one or more of the versions of iPhone 12), which LiDAR scanner can accurately judge distances and therefore depth, and allows for improved augmented reality. These cameras and scanners would be looking inward at the eyes of the Subject.

In addition, the Special Input Eyeglasses will have a "speaker/headphone/earphone" and microphone (which may-or-may not use the functionality of the smartphone or its equivalent [as a headphone wirelessly or by wire connected to a smartphone does today], depending on the type of Special Eyeglasses being used), so the Subject/wearer can hear commands (e.g., from a Professional or AI-powered chatbot) and speak responses (e.g., to a Professional or an AI chatbot).

If the invention's input device of Special Input Eyeglasses with inward facing cameras is used, aimed at an unconscious Subject/wearer's eyes (which have been opened and are kept open with a speculum, and those Special Eyeglasses have the ability to add or subtract light (i.e. light can be shined into the Subject's eyes, and the light can be turned on-or-off with varying intensity, et al.), assessment of the unconscious Subject's pupil size, shape, and equality before and after exposure to light can easily be performed with great speed, objectivity, and accuracy. The invention can assign a partial GCS score based on the portions of the test based on Subject eyes response data and Subject verbal response data.

The Special Input Glasses may also have many of the same functionalities as the AR Output Glasses, AR Output Goggles, and/or the VR Output Headsets (each described in Section III (D) below) to enable various types of visual testing of the Subject.

The Special Input Glasses may also have an AI-powered chatbot (audio input and output). The invention's AI-powered chatbots can assist in providing audio input and audio data output for the benefit of the Subject.

For the Subject, for example but without limitation, the invention chatbot can ask questions, make commands, or attempt to inform the Subject of specified information. All of these audio outputs are programable and optional. Human Professionals could substitute for the invention chatbot.

7. Special Input Goggles with Cameras Looking Inward at Eyes of the Subject/Wearer ("Special Input Goggles").

The Special Input Goggles have cameras looking inward at the eyes of the Subject/wearer. It should be noted that the Subject/wearer can be an animal or a human. Amazon.com currently sells various brands of:
  (x) goggles for dogs (as sunglasses, and, for example, for UV protection, wind protection, dust protection, and fog protection), although none of the uses are for the purposes of the invention.
  (y) goggles for horses (for bright Sun Eye sensitivity, protection from UV, dust, wind, debris, branches, and twigs while riding, and protection for uveitis, eye injury, scratch, corneal ulcer, infection, blindness, and eye cancer), although none of the uses are for the purposes of the invention.

There are three types of Special Input Goggles:
  (i) Those that are wirelessly connected to a smartphone or its equivalent (similar to the first generation Apple Watch as an example of similar functionality), in which the Special Goggles themselves would lack internet connectivity, and most if not all of the data is processed in the smartphone or its equivalent. These Special Input Goggles would run on batteries that could be charged wirelessly, but optionally could be connected to a power main.
  (ii) Those that can function as a purely standalone device, with no need for a smartphone or its equivalent for functionality. These Special Input Goggles could run on batteries that could be charged wirelessly, or could be connected to a power main.
  (iii) Those that are tethered to a PC or non-smartphone (i.e., more powerful) computer for functionality. These Special Input Goggles could run on batteries that could be charged wirelessly, or could be connected to a power main.

The Special Input Goggles may have a laser-powered 3D camera (rumored for inclusion in one or more of the versions of iPhone 12), and/or a LiDAR scanner (a form of which is currently found in the iPAD Pro 2020, and which is rumored for inclusion in one or more of the versions of iPhone 12), which LiDAR scanner can accurately judge distances and therefore depth, and allows for improved augmented reality. These cameras and scanners would be looking inward at the eyes of the Subject.

In addition, the Special Input Goggles will have a "speaker/headphone/earphone" and microphone (which may-or-may not use the functionality of the smartphone or its equivalent [as a headphone wirelessly or by wire connected to a smartphone does today], depending on the type of Special Input Goggles being used), so the Subject/wearer can hear commands (from a Professional or AI-powered chatbot) and speak responses (to a Professional or AI-powered chatbot).

The Special Input Goggles, with cameras looking inward at the eyes of the Subject/wearer, are ideal for use on Subjects who are unconscious, comatose, or undergoing general anesthesia. [This is discussed later.]

The Special Input Goggles will enable Professionals to view and monitor the Subject's eyes so as to use the invention's cameras, transceivers, computer hardware and software, and output devices to (i) measure eye movements and/or other Eye data of the Subject to assist and lessen the burden of the first responder/Professional, all the while protecting the Subject's eyes, and (ii) determine when the Subject's eyes need irrigation, and automatically irrigating the Subject's eyes when appropriate.

a. Two Versions of the Special Input Goggles. The Special Input Goggles have two different versions, the "transparent Special Input Goggles" and the "sealed Special Input Goggles".
    (i) Transparent Special Input Goggles.

In one embodiment of the invention the Special Input Goggles will have a transparent front so that Professionals (e.g., first responders, or in an emergency room or an operating room) can see through them. The transparent front of the goggles allows the Professionals to not be solely reliant on the invention's video output cameras for certain issues.
    (ii) Sealed Special Input Goggles. In another similar embodiment of the invention the Special Input Goggles will have a sealed/closed, non-transparent front, and Professionals will rely solely on the invention's video output from the sealed Special Input Goggle's cameras.

An alternative variation is Transparent Special Input Goggles that can in seconds convert to Sealed Special Input Goggles, by alternative means known to those skilled in the art, such as, by without limitation, using crystals that when charged can change light entry, adding a black cover over the Transparent Special Input Goggles, et al.

b. Use of an Eyelid Speculum. To take advantage of the benefits of the Special Input Goggles on a Subject who is unconscious, comatose, or undergoing general anesthesia, before placing the Special Input Goggles on the Subject, the Subject's eyelids are held open with an eyelid speculum, which eyelid speculum remains in place while the Special Input Goggles are on the Subject. A local anesthetic eye drop may be used on the Subject prior to placing the eyelid speculum on the Subject to remove the feeling of discomfort of the eyelid speculum.

c. Internal Nozzle. The Special Input Goggles will have as part of them an internal nozzle to irrigate the Subject's eyes being held open by an eyelid speculum as needed, as determined by the computer software program of the invention. The Special Input Goggle's internal nozzle is connected by a hose to a reservoir container outside the Special Input Goggles, which reservoir container holds a sterile cleaning solution for the ophthalmic irrigation of the Subject's eyes, and a pump (either inside or outside the reservoir container) which pumps/squirts the sterile eye irrigation solution from the reservoir container to the nozzle to the Subject's eyes in liquid (a drip) or spray (a mist) form. If deemed necessary based on duration of use of the eyelid speculum, a local anesthetic eye drop may be placed in the Subject's eyes using the same or a separate nozzle as that used for application of the sterile eye irrigation solution for the ophthalmic irrigation of the Subject's eyes.

d. Sterile and Firm Fit. The edges of the Special Input Goggles, and the Special Input Goggles themselves, need to be sterile or sterilized immediately prior to use (for a prior relevant period of time with ultraviolet light and/or other appropriate means, such as using ozone, as is typically done with sleep apnea masks). The edges of the Special Input Goggles need to fully touch the face of the Subject with no gaps, similar to how sleep apnea masks cover a user's nose and mouth during sleep.

e. Special Input Goggles "Commencement of Use" Timing. The time to put the sterilized eyelid speculum on the Subject (including potentially first adding a local anesthetic drop in the Subject's eyes), and then putting the sterilized Special Input Goggles on the Subject, typically should take no more than a minute or two, making it ideal for the earlier described Subject situations for which it is intended.

Some versions of the Special Input Goggles may also have many of the same functionalities as the AR Output Glasses, AR Output Goggles, and/or the VR Output Headsets (each described in Section III (D) below) to enable various types of visual testing of the Subject.

The invention's AI-powered chatbots can assist in providing audio data output for the benefit of the Subject and/or the Professional. For the Subject, for example but without limitation, the invention chatbot can ask questions, make commands, or attempt to inform the Subject of what is going on. For the Professional, for example but without limitation, the invention chatbot can provide audio information of Subject data re Subject cognitive condition based on Subject eye movements, et al. All of these audio outputs are programable and optional.

8. Fixed Camera-Type Device(s)

Everything done with the Device (as described in III (A)(1) above) can be done with a portable-but-fixed input device that can be affixed/attached/fastened/hung over a doorway or on a wall et al., in a Subject's residence, or over a door, by a feeding area, et al. in where an animal or animals is kept. The input device would have all the necessary functionalities as earlier described.

Examples of uses, without limitation of this type of invention portable-but-fixed input device include:
  (i) Camera(s) fixed at the "doorways"/entryways of animal barns, pens, or shelters (this is automatic Eye data capture);
  (ii) Camera(s) fixed in animal feeding areas, animal stalls and/or holding/sleeping areas (this is automatic Eye data capture);
  (iii) Camera(s) fixed on or near the outside wall of an aquarium, or in the water fixed near or on the aquarium floor, roof, or inside wall of the aquarium (this is automatic Eye data capture);
  (iv) Camera(s) attached to fixed areas underwater (for example, without limitation, attached to a net and/or tethered to a dock, the side of a river, stream, lake and/or pond), that can capture, as part of the invention system, and as a means to implement its methodology, the Eye data of fishes of various types (this is automatic Eye data capture).

9. Laptop/Desktop Computer (with Built-in or "Clip-On"/Attachable Camera(s)).

Everything done with the Device (as described in III (A)(1) above) can be done with a laptop or desktop computer, which, if it does not have a built-in camera (or one with sufficient capacity) can use one or more clip-on/attachable cameras (with sufficient resolution, magnification and frames per second ability, et al.). That type of input device would have all the necessary functionalities as earlier described.

10. Drone Camera Input (the "Special Input Drone").

Everything done with the Device (as described in Section III (A)(1) above) can be done with a drone, assuming it has one or more cameras with sufficient magnification and frames per second ability, et al. The Special Input Drone input device would have all the necessary functionalities as earlier described with the Device in Section III (A)(1) above. Alternatively, the Special Input Drone can wirelessly send and receive information to and from the smartphone or its equivalent (or directly to it if it is attached), in the same manner as the first generation Apple Watch.

There are two types of Special Input Drones: the "in-the air Special Input Drone" (the "Invention Air Drone"), and the "in-the-water/underwater Special Input Drone" (the "Invention Water Drone").

The Invention Air Drone:
  (i) Is ideally used for examining and monitoring the eyes of various types of non-fishes animals outdoors, such as, without limitation, cattle, pigs, sheep, horses, et al. There are AR see-through smart glasses in the commercial marketplace (such as for example, without limitation, the Epson Drone Soar Application/Epson Moverio BT-300), which are optimized to assist in piloting air drones and making it easier to capture desired images and videos.

Camera(s) on the Invention Air Drone can capture, as part of the system of the invention and as a means to implement its methodology, the Eye data of, for example:
  (a) Beef cattle in a cattle yard or on an open range;
  (b) Pigs in the yard of a pig-pen or a more open area;
  (c) Free-range chickens (or other human-raised fowl, such as ducks or turkeys) that are outdoors (be it in a chicken yard or, for example, in a pasture); or
  (d) Horses outdoors (in a coral or on a more open range).

Dependent on how programmed and used, this embodiment of the invention can be automatic Eye data capture, or it can be manual or semi-automatic Eye data capture). The Air Drone has a transceiver that works in a manner known to those skilled in the art The Invention Water Drone:
  (i) Can examine and monitor the eyes of various types fishes in bays, rivers, streams, lakes, seas, or oceans, either in fish farms or in the wild. It can look down on them or travel underwater with them.

Note: There are existing commercial battery-powered wireless water surface and underwater drones in the commercial marketplace which are equipped with cameras so one can see and record professional still underwater photos and WiFi live-streaming video to one's smartphone or VR Headset (although not for the purpose of the invention).
  (ii) Will have a transceiver that works in a manner known to those skilled in the art.

Camera(s) on the Invention Water Drone can capture, as part of the system of the invention and as a means to implement its methodology, the Eye data of fishes (and other underwater animals) of various types (including without limitation fishes that are on fish farms or in the wild, be it in streams, rivers, ponds, lakes, seas, or oceans).

Dependent on how programmed and used, this embodiment of the invention can be automatic Eye data capture, or it can be manual or semi-automatic Eye data capture.

The Special Input Drone (i.e., both the Invention Air Drone and the Invention Water Drone):
  (i) Can use eye-tracking software and can identify a specific animal by its iris if the animal has been previously identified by the invention (and if the animal's iris is visible). Hence, the invention can in a sense be used for contactless, non-tagged animal tracking as well as for animal health matters.
  (ii) Will have and use sensors to determine its distance from objects (including animals), both to navigate to avoid collisions and to perform its mission of collecting and monitoring animal Subject eye data.
  (iii) Will have the ability to operate in a manual or autonomous mode, with speed controls.
  (iv) Will have the ability to automatically return to base (so it does not crash or become lost before its energy source expires).
  (v) May or may not have lights on it (with various light functionalities, such as the ability to turn a bright light on-and-off, having a blinking light, et al.) for travel identification, assisting with better camera imaging to better observe animal Subjects, and/or performing certain eye tests on the animal Subjects' eyes.
  (vi) Will use Edge AI or "pure cloud" for processing data. The data may also be processed in the "unit" that remains with the controller of the Special Input Drone (assuming there is one).

The drone portion of the Special Input Drone can be powered/fueled by power sources/fuel sources known to those skilled in the art, including without limitation:
  (i) For the Invention Air Drone: electric/battery (e.g., without limitation, a lithium polymer battery), electric/solar, hydrogen fuel cell, combustion (using, for example, without limitation, kerosene or gasoline), or tethered to a power supply.
  (ii) For the Invention Water Drone: electric/battery (e.g., without limitation, a lithium polymer battery), electric/solar, hydrogen fuel cell, combustion (using, for example, without limitation, kerosene and/or gasoline or other carbon-based combustible), water flows/currents, or tethered to a power supply.

Note: Invention Air Drones could fly over outdoor crowds of human Subjects in order to obtain various types of information on potential diseases carried by Subjects in the crowd, especially contagious diseases (for example, without limitation, such as Covid-19), to use big data to measure the prevalence and spread of the disease, as well as to use the collected data for other aspects of potential disease control (such as notifying individual human Subjects who may be individually identified as possibly having the condition) (all within the confines of whatever relevant laws are applicable).

For each of the input devices that are part of the invention (as described above and herein), the invention may optionally use an optional additional auxiliary input device that measures and collects human or animal body temperature data by means known to those skilled in the art. In one embodiment, this can use an electronic thermometer appropriate for the area of the human body part or animal body part from which the temperature will be measured) (the "Auxiliary Input Device"). In an embodiment, are two versions of the Auxiliary Input Device: (i) a standalone Auxiliary Input Device, in which all functionality (e.g., temperature data measurement and collection, as well as transceiver and battery power) resides in the Auxiliary Input Device, and (ii) an Auxiliary Input Device that works wirelessly or by wire together the invention input device with which the Auxiliary Input Device is an additional auxiliary input device, in which some of the technology is in the Auxiliary Input Device, and some is in the invention input device, and they work together, with the Auxiliary Input Device piggy-backing off the transceiver and battery of the invention input device, et al.

Ideally the Subject's eye data and temperature data can be synchronized in time in a statistically meaningful manner by a means known to those skilled in the art (including without limitation the use of "if-then" and/or AI software in the cloud or "if-then" and/or EDGE AI software located in the EDGE) and the Subject's temperature data and the Subject's eye data may be cross-compared and correlated, and if statistically relevant can potentially clarify and strengthen "indications of Conditions" of the Subject, including the trends and the speed of the trends related thereto, and thereby allow for potentially better facilitation of both acute and long-term treatment and therapy adjustments).

B. Cameras on Input Device(s)

Like computer chips before them, cameras are becoming better, cheaper, and smaller every year. The heavy atoms in cameras (i.e., the hardware bulk) will continue to be replaced by weightless software, and over time the laws of light will govern what is possible.

1. Cameras.
    a. Invention Camera-Types. The types of cameras or camera-like devices that are part of the invention and used by it are set forth and generally described in ANNEX K and ANNEX L. That said, there may be similar stand-alone digital cameras sending data through their own or separate transceivers, as well as different cameras not described in ANNEX K and ANNEX L.
    b. Known Condition or Risk for Known Condition. Envision a person with an identified/diagnosed specific Condition (e.g., without limitation, diabetes, or high blood pressure) or at high risk for a specific Condition. That person would want to use the invention with an input device with a camera that could monitor them for that specific Condition. They could simply obtain an input device with an appropriate camera and the rest of the invention would function as it does, although it could specifically focus on their particular Condition of concern, while still "looking" for new potential Condition.

For example, a person with diagnosed diabetes would want an input device with a camera that could examine and monitor parts of their eyes that indicate (i) cataracts, (ii) glaucoma, and (iii) diabetic retinopathy, the three (3) most common eye diseases which most diabetics may develop. The reverse is true as well: a person with indications of (i) cataracts, (ii) glaucoma, or (iii) diabetic retinopathy may also have or should beware of getting diabetes.

c. Cameras and Sensors Used for 3D, VR and AR. The embodiment uses sensors such as LiDAR (a form of LiDAR scanner is currently found in the iPAD Pro 2020, and is rumored for inclusion in one or more of the versions of iPhone 12), which LiDAR scanner can accurately judge distances and therefore depth, and allows for improved augmented reality, and lasers. A laser-powered 3D camera is rumored for inclusion in one or more of the versions of iPhone 12.

2. Remote Control Potential By Professional of Invention Input Devices/Cameras (Hand-Off).

The invention's input devices/cameras, in certain modes, which are examining and reviewing the eyes of Subjects, may be controlled remotely by Professionals.

One type of invention input device can have either one, or more than one, type of camera on it, with each type of camera allowing for the capture of data from different parts of a Subject's eyes. Various types of cameras used as a part of the invention, without limitation, are set forth in Annex K.

If additional Subject eye data is needed (more than can be captured on an input device with its camera(s)), the same input device with a different type of camera or cameras can be used.

For example, without limitation, there are many different types of cameras that can work together with an iPhone, as set forth in Annex K.

Use of Smartphone Cameras for Clinical Data Acquisition for Teleophthalmology: The Need for Appropriate Calibration to Ensure Accurate Objectivity.

Today's AI-powered filters, such as the built-in ones on Instagram and Facebook, do a decent job of adjusting contrast and lighting and even adding depth-of-focus effects to simulate an expensive lens.

Indeed, use of smartphone cameras attached to ophthalmic imaging systems enables the acquisition of high-quality images of the eye in a simple and affordable manner, given that smartphones are convenient and portable and their wireless connection provides for an easy Internet connection.

Use of smartphone cameras for clinical data acquisition for teleophthalmology, however, without adequate information of the quality of images can compromise data accuracy and repeatability. Calibration of a smartphone's camera is essential when extracting objective data from images.

It is well-known that two different cameras, or even the same camera with different settings, give different images for the same scene, which are possibly different to those perceived by a human's visual system.

One reason is the responses of the camera sensors vary from one camera to another. The red, green, and blue (RGB) values given by any imaging system are device dependent, and are different from the responses of human retina cells, and subsequent interpretation by the human brain. Also, camera makers have their own camera-specific and proprietary imaging processing algorithms, including autofocus algorithms that attempt to automatically enhance the perceptual image quality of the images. Autofocus mode adds lack of control and introduces uncertainty of color reproductions of clinical images obtained with different smartphones.

Accordingly, it is important to control for a camera's type and lighting levels when extracting objective data, so when comparing data an "apples-to-apples" comparison can be made. Appropriate compensation must be made for pictures taken with different cameras if they are not calibrated and they have different pixel size, sensor size, sensitivity, and optics.

The application of white balance and color correction to each image obtained under certain illumination conditions and with one specific camera is a standard procedure to obtain the color ground truth of the scene being photographed. Any differences between lighting levels and camera types tend to be significantly minimized (but not made a perfect match) after cameras are calibrated.

Overall, a smartphone's camera calibration is essential when comparing images of the eye obtained with different smartphones and/or lighting levels by means of objective metrics.

The human eye, evaluating clinical eye images, is not affected by calibration, type of smartphone camera and/or lighting level due to the human eye property of color constancy. The differences are generally not noticed, and pattern comparisons between and among eye images are subjective.

(https://www.nature.com/articles/s41598-018-37925-5)

An embodiment detects or is otherwise told the specific type of camera (and or smartphone or its equivalent) from where Subject eye data is coming, and equalize calibration and light as appropriate and to the extent necessary, in a manner known to those skilled in the art, so meaningful objective data comparisons can be made for the purpose of the invention.

The Non-User Input Portion of the Invention: The Cloud and Thereafter

The non-end user input portion of the System (the end on which the streaming video of the eyes and/or eye movements of the user are received) is initially transmitted to the user's account in a cloud (the "Cloud"), where the data from the Device resides.

In the Cloud, depending on the user's application software, pre-specifications:

1. User's eyes-data is forwarded to the computer of user's pre-selected Professional, in real-time, near real-time, or delayed time, for examination.

2. User's eyes-data is reviewed by machine learning software, comparing the data to:
    (i) prior eyes-data of the user, and/or
    (ii) eyes-data of other users contextually similar to the user, and/or
    (iii) eye data of "healthy eyes",
  and after analysis, a report is sent to (x) the user, or (y) user's pre-selected Professional, or (z) both.

3. User's eye data is reviewed by deep learning software, and after analysis, a report is sent to (x) the user, or (y) user's pre-selected Professional, or (z) both.

Eye Monitoring Service: Software Architecture

Figure 4:
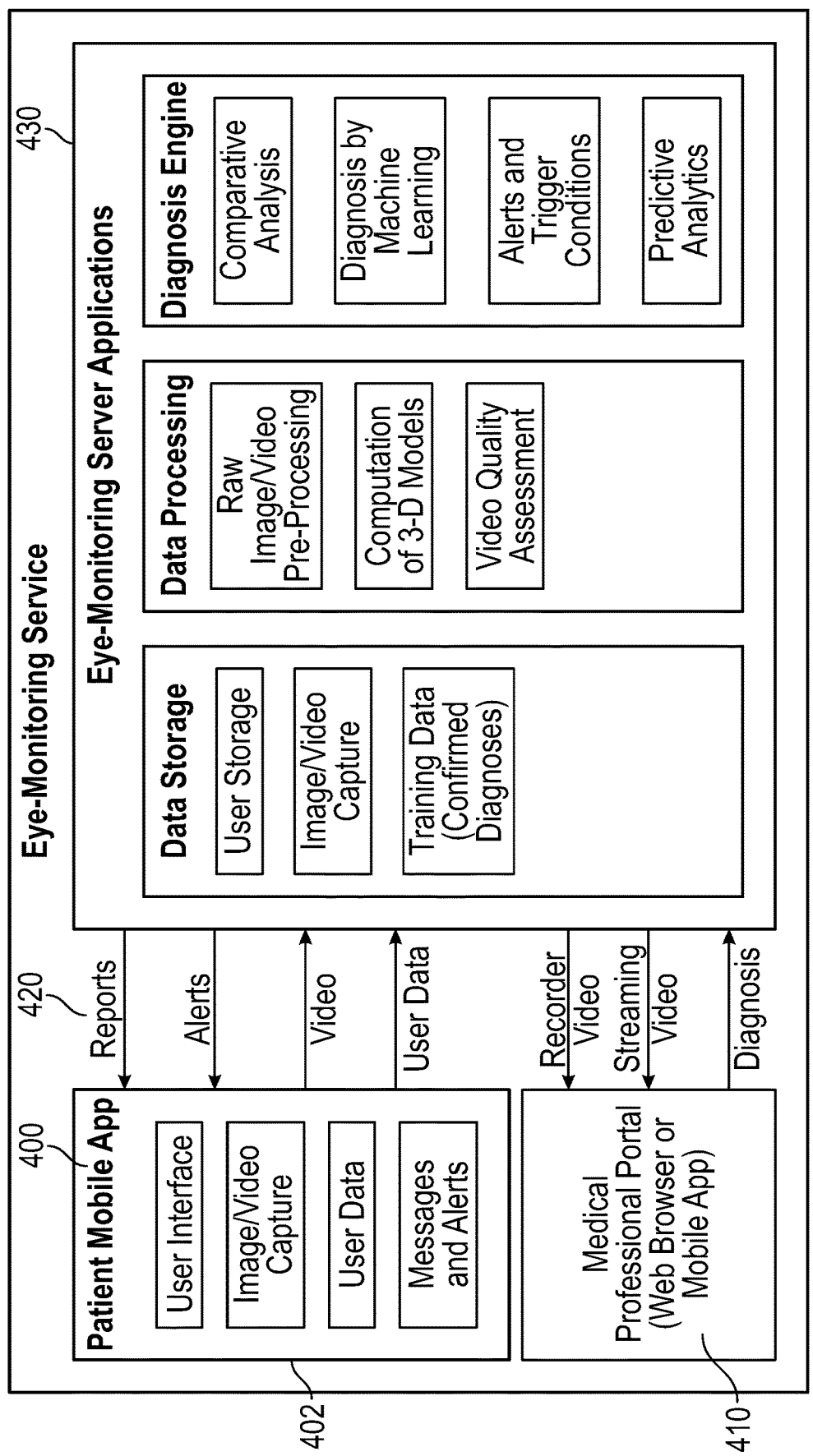
FIG. 4 shows a block diagram of an eye monitoring service.

The software components included in one embodiment of the eye-monitoring service are depicted in FIG. 4.

First, this embodiment of the invention includes a Subject/Patient Mobile App 400 that runs on a user's handheld computing device 402 such as a smartphone or small tablet. The Subject/Patient Mobile App may be acquired from an online app marketplace, such as the Apple App Store or Google Play. The Subject/Patient Mobile App includes several subcomponents. A user interface subcomponent implements the menus, graphics, buttons, and data displays with which a user interacts when the Subject/Patient Mobile App is active. An image/video capture subcomponent implements logic for initializing the device camera, configuring the camera's settings to increase captured image quality, capturing raw images, and storing images to the flash memory of the mobile device. A user data component is responsible for storing information about the current Subject/patient user, such as the unique identifiers that associate the user with medical records and provider information that are stored securely within the server-side applications and databases of the eye-monitoring service.

Using the Subject/Patient Mobile App, a Subject/patient can enroll or register in the eye-monitoring service. Optionally, the eye-monitoring service may be configured to restrict enrollment to Subject/patients who have been invited by a medical provider. A user who has successfully enrolled in the service is able to log in to the Subject/Patient Mobile App using standard means, such as a password, fingerprint, or facial or iris recognition. Once logged in, a Subject/patient can view a variety of data that has been collected, stored, or generated by the eye-monitoring service. For example, a Subject/patient can view images and videos that have been collected using the Subject/Patient Mobile App. Similarly, a Subject/patient can view past and current alerts and notifications generated by the eye-monitoring service. A Subject/patient can also review messages sent to or received from the Subject/patient's medical provider. A Subject/patient can also initiate new correspondence with his or her medical provider. Depending on the configuration of the eye-monitoring service, a Subject/patient may also be able to initiate the capture of a new eye image or video. Also depending on the configuration of the eye-monitoring service, a Subject/patient may be able to view health metrics and evaluations generated by the eye-monitoring service.

Second, this embodiment of the invention includes a Medical Professional Portal 410 that may be accessed through a web browser or mobile app. For example, a medical professional may opt to access the Medical Professional Portal through a web browser when in an office setting that includes desktop and laptop computers, and the medical professional may opt to access the Medical Professional Portal through a mobile app at other times and locations.

Using the Medical Professional Portal, a medical professional may, for example, view a list of patients whose medical information the medical professional is authorized to view. The medical professional may view records associated with these patients, such as the patient's demographic and medical information as well as images and videos the patients' eyes that have been captured by the eye-monitoring system. The medical professional may also view current and past alerts that have been generated by the eye-monitoring system. The medical professional may also view the results of automated analyses and assessments performed by the eye-monitoring system. For example, the medical professional may view in a table, graph, or other format the changes that have occurred to the patient's eyes over a period of time. The medical professional may similarly view risk metrics and scores produced by the eye-monitoring system.

Both the Subject/Patient Mobile App and the Medical Professional Portal are connected via an Internet connection 420 to a collection of Eye-Monitoring Server Applications 430 that run on server computers. The Subject/Patient Mobile App and Medical Professional Portal exchange a variety of information with the Eye-Monitoring Server Applications using an encrypted, secure data transmission protocol, such as HTTPS. For example, when a new Subject/patient user registers for the service or changes information in his or her profile, including medical information, the Subject/Patient Mobile App uploads the patient information to the Eye-Monitoring Server Applications where it is added or updated within a secure data storage system. As another example, when a new image or video has been captured by the Subject/Patient Mobile App, the Subject/Patient Mobile App uploads the image(s) and video(s) to the Eye-Monitoring Server Applications. Similarly, when a medical professional selects to view a Subject/patient's information or eye images or videos using the Medical Professional Portal, the information is securely downloaded from the Eye-Monitoring Server Applications to the Medical Professional Portal.

The Eye-Monitoring Server Applications include applications and programs for processing and analyzing eye images and videos in a variety of ways. One server application performs pre-processing of raw images and videos received from the Subject/Patient Mobile App. This application reads metadata associated within the image or video, including the video format, resolution, creation time, patient name and ID, and so on, and inserts a record containing this information in a database.

Another server application processes the images and videos to assess their quality. This application analyzes the videos to determine the position of the eyes within the image or video and evaluates whether the lighting, color, clarity, and stability in the image or video are acceptable. This server application may also include the capability to improve the image or video in various ways. For example, this server application may crop out portions of the image or video that do not contain the eyes or are not otherwise useful. The server application may attempt to adjust image characteristics such as white balance. The server application may run a stabilization algorithm on a video to reduce shakiness and keep the position of the eyes in the video constant. When an image or video is received that does not pass the quality assessment, and the quality cannot be improved through the mechanisms described, the server application may generate an alert or notification that is transmitted to the Subject/Patient Mobile App advising the Subject/patient that the image or video was unusable and a new image or video should be captured.

Another server application implements algorithms for generating models and measurements of the Subject/patient's eye and eye parts (i.e., Eye data). This server application may compute measurements of the size and shape of the eye, eyelid, iris, pupil, and/or retina. This server application may also characterize the color of the eye (e.g., redness or yellowness); the presence and position of blood vessels; or the presence of other anomalous structures. This server application may be configured to compute specific models and measurements for particular users and may be calibrated based on past images, videos, models, and measurements stored within the eye-monitoring service's databases.

Other server applications are responsible for performing diagnostic analyses. These diagnostic applications are configured to assess the risk or probability that a Subject/patient has a particular medical condition or the severity of a known medical condition has changed. One diagnostic application may be programmed to perform comparative analyses, in which images, videos, models, or measurements of a Subject/patient's eyes are compared with past images, videos, models, or measurements of the same patient, a known healthy patient, or a known diseased patient. Such an application may, for example, determine whether the Subject/patient's eyes have changed in shape or color or whether new anomalous structures have appeared.

While the patent application as described herein describes carrying out certain diagnoses, it should be understood that this encompasses not only carrying out the diagnosis, but also providing an indication of the data from which a diagnosis could be carried out either by another computer, or by a professional. It is envisioned that certain aspects of this invention could hence be embodied without receiving FDA approval for the diagnosis.

Another diagnostic application may be programmed to use machine learning techniques to quantify the risk that a Subject/patient has a particular condition based on an image or video of the Subject/patient's eye. The machine-learning-based diagnostic application may be constructed using supervised learning techniques, in which a machine learning algorithm is supplied with training data to classify inputs. In the eye-monitoring service, a diagnostic application that uses supervised machine learning may use the images and videos collected by the Subject/Patient Mobile App, eye models and measurements computed from those images and videos, and medical and demographic information provided by the Subject/patient or medical provider to classify Subject/patients as high risk or low risk for a particular condition. The diagnostic application may also provide a probability distribution describing the risk of a particular Subject/patient for a particular condition. The training data needed by the supervised machine learning algorithm may be provided in the form of a dataset that has been collected external to the eye-monitoring service, but in the preferred embodiment the eye-monitoring service is able to use its own collected data as training data. For example, if the eye-monitoring service collects images of a Subject/patient's eyes and subsequently the Subject/patient is diagnosed in a medical professional's office with a particular Condition, this finding can be fed back into the eye-monitoring service as a data point for training the supervised machine learning algorithm.

The machine-learning-based diagnostic application may also be constructed using unsupervised machine learning techniques, which are helpful for finding undiscovered patterns in data. Unsupervised learning may be used to cluster patients into similar groups based on eye images, videos, models, measurements, demographic data, and medical history. This analysis may then indicate previously unknown patterns in the data or identify outliers that, along with the subject matter expertise of medical professionals, could be used to improve diagnoses of eye conditions or other conditions that affect the eye. For example, if the cluster analysis produces a cluster of patients among which the incidence of a condition is higher than normal, it may indicate that some characteristic of that group is associated with elevated risk for the condition.

The eye-monitoring service is designed as an extensible platform such that new data processing and diagnostic applications may be "plugged-in" over time. If medical researchers develop a new diagnostic engine for a particular disease based on image processing and machine learning techniques, that engine can be plugged-in to the eye-monitoring service through the use of standard interfaces and software adapters. For example, the eye-monitoring service may optionally be implemented using web services and protocols that allow for individual components and application to be inserted and removed from the system over time.

These additions may include:
(x) non-eye "health data" of the Subject which, through means and techniques known to those skilled in the art the invention can input and cross-compare and cross-reference with
(y) the eye data of the Subject (as obtained and processed by the invention),
to potentially reach a more dispositive probability of the indication of a Subject's Condition and/or trend and speed of the trend of a Subject's Condition (thereby potentially better facilitating for the Subject both acute and long-term therapy adjustments).

For example, non-eye "health data" of the Subject may include (without limitation):
(1) Blood Analysis—Subject blood analysis data can be obtained from a clinical laboratory, such as Quest Diagnostics. Hundreds of hematological tests and procedures have been developed, and many can be carried out simultaneously on one sample of blood with such instruments as autoanalyzers (which are discussed below). Such tests for a subject typically need to be ordered by a physician, and physicians generally place great reliance on the results of such tests. Blood tests may include, without limitation:
(a) blood count—A complete blood count (CBC) is a blood test used to evaluate your overall health and detect a wide range of disorders, including anemia, infection, and leukemia. A complete blood count test measures several components and features of your blood, including: (i) red blood cells, which carry oxygen, (ii) white blood cells, which fight infection, (iii) hemoglobin, the oxygen-carrying protein in red blood cells, (iv) hematocrit, the proportion of red blood cells to the fluid component, or plasma, in your blood, (v) platelets, which help with blood clotting.

Abnormal increases or decreases in cell counts as revealed in a complete blood count may indicate that you have an underlying medical condition that calls for further evaluation. [See generally https://www.mayoclinic.org/tests-procedures/complete-blood-count/about/pac-20384919].
(b) blood typing—Blood type is comprised of two blood groups: ABO and Rh Blood types are based on antigens on the surface of your red blood cells. An antigen is a substance that triggers an immune response by your body against that substance. Blood typing is typically done by a phlebotomist. A phlebotomist (someone trained to draw blood) will use a needle to draw blood from your arm or hand at your doctor's office, a clinical laboratory, or a hospital. Alternatively, there are at-home blood typing tests.

With at-home blood typing tests, they typically ask that you prick your finger with a lancet and put drops of your blood on a special card. After putting the blood on the card, you can observe the areas where blood clumps or spreads out, and then match those reactions to an included guide. Some home testing kits have vials of fluid for your blood, as opposed to a card. [See generally https://www.healthline.com/health/how-to-find-out-your-blood-type #blood-testing].
(c) bone marrow aspiration—Bone marrow aspiration is a procedure that involves taking a sample of the liquid part of the soft tissue inside your bones. Bone marrow is the spongy tissue found inside bones. It contains cells that produce white blood cells (WBCs), red blood cells (RBCs), and platelets inside larger bones. Conditions and diseases related to bone marrow problems include: (i) anemia, which is a low red blood cell count, (ii) bone marrow diseases, such as myelofibrosis or myelodysplastic syndrome, (iii) blood cell conditions, such as leukopenia or polycythemia vera, (iv) cancers of the bone marrow or blood, such as leukemia or lymphoma, (v) hemochromatosis, which is a genetic disorder in which iron increases in the blood and builds in organs and tissues, (vi) infection, especially chronic diseases like tuberculosis, and (vii) storage diseases, such as amyloidosis or Gaucher's disease. Bone marrow aspiration can be an important test if one is having cancer treatment, as it can help determine if the cancer has spread to the bones. [See generally https://www.healthline.com/health/bone-marrow-aspiration #purpose].

(d) cephalin-cholesterol flocculation—A cephalin-cholesterol flocculation test is a laboratory test for the nonspecific measurement of blood globulins, a group of proteins that appear in abnormally high concentrations (hyperglobulinemia) in association with certain diseases. The test consists of adding blood serum to a suitably prepared emulsion of cephalin-cholesterol. A flocculent precipitate will form if the serum is abnormally high in globulins.

The test is helpful in confirming the presence of liver disease, subacute bacterial endocarditis, rheumatoid arthritis, and malaria. [See generally https://www.britannica.com/science/cephalin-cholesterol-flocculation].

(e) enzyme analysis—Enzyme analysis, in blood serum, is a measurement of the activity of specific enzymes in a sample of blood serum, usually for the purpose of identifying a disease. The enzymes normally are concentrated in cells and tissues where they perform their catalytic function; in disease, however, certain enzymes tend to leak into the circulation from the injured cells and tissues. More than 50 enzymes have been found in human serum. [See generally https://www.britannica.com/science/enzyme-analysis].

(f) epinephrine tolerance test—An epinephrine tolerance test is an assessment of the metabolism of liver glycogen by measuring the blood-sugar response to a standard dose of epinephrine (adrenalin).

Individuals with liver disease or with an inherited deficiency of the enzymes that degrade glycogen to glucose show subnormal response. [See https://www.britannica.com/science/epinephrine-tolerance-test].

(g) glucose tolerance test—The glucose tolerance test is a medical test in which glucose is given and blood samples taken afterward to determine how quickly it is cleared from the blood. The test is usually used to test for diabetes, insulin resistance, impaired beta cell function, and sometimes reactive hypoglycemia and acromegaly, or rarer disorders of carbohydrate metabolism. [See generally https://en.wikipedia.org/wiki/Glucose_tolerance_test].

(h) hematocrit—A hematocrit test measures how much of your blood is made up of red blood cells. Red blood cells contain a protein called hemoglobin that carries oxygen from your lungs to the rest of your body. Hematocrit levels that are too high or too low can indicate a blood disorder, dehydration, or other medical conditions. [See generally https://medlineplus.gov/lab-tests/hematocrit-test/].

(i) immunologic blood test—An immunologic blood test is any of a group of diagnostic analyses of blood that employ antigens (foreign proteins) and antibodies (immunoglobulins) to detect abnormalities of the immune system. Immunity to disease depends on the body's ability to produce antibodies when challenged by antigens. Antibodies bind to and help eliminate antigens from the body. The inability of the body to produce certain classes of immunoglobulins (IgG, IgA, IgM, IgD, IgE) can lead to disease. Complexes formed by the antigen-antibody reaction can be deposited in almost any tissue and can lead to malfunction of that organ. [See generally https://www.britannica.com/science/immunologic-blood-test].

(j) inulin clearance—Inulin is a sugar found in plants that is poorly digested by humans. It is used to estimate the health of the kidneys by assessing their ability to filter inulin from blood, after it has been administered. The Inulin Clearance Blood Test helps determine the inulin clearance rate, which is the rate at which insulin leaves blood. It helps assess kidney function. [See https://www.dovemed.com/common-procedures/procedures-laboratory/inulin-clearance-blood-test/].

(k) liquid biopsies—These tests pick up genetic material shed by cancer tumors into the blood. For now, these blood-based tests are used not to screen for cancer in healthy subjects but to guide treatment in those who have already been diagnosed. [See generally A. Park, "Why doctors are turning to blood to learn more about tumors", Time, vol. 196, no. 15, 2020, at p. 25.]

(l) serological test—Also called serology test or antibody test, a serological test is any of several laboratory procedures carried out on a sample of blood serum (the clear liquid that separates from the blood when it is allowed to clot) for the purpose of detecting antibodies or antibody-like substances that appear specifically in association with certain diseases. There are different types of serological tests—for example, flocculation tests, neutralization tests, hemagglutinin-inhibition tests, enzyme-linked immunosorbent assays (ELISAs), and chemiluminescence immunoassays. Serological testing is particularly helpful in the diagnosis of certain bacterial, parasitic, and viral diseases, including Rocky Mountain spotted fever, influenza, measles, polio, yellow fever, and infectious mononucleosis. It is also useful in the detection of autoantibodies (harmful antibodies that attack components of the body) that are involved in autoimmune diseases, such as rheumatoid arthritis. As a practical mass-screening tool, serological testing has proved valuable in the detection of diseases such as syphilis, HIV/AIDS, and epidemic and pandemic infectious diseases (e.g., influenza and coronavirus disease). [See generally https://www.britannica.com/science/serological-test].

(m) thymol turbidity—Thymol turbidity is a laboratory test for the nonspecific measurement of globulins, a group of blood proteins that appear in abnormally high concentration in association with a wide variety of diseased states, notably those affecting the liver. The test consists of adding 1 volume of blood serum to 60 volumes of a buffer supersaturated with thymol; the thymol-globulin interaction results in turbidity, the degree of which varies with the concentration of globulins. High turbidity is observed in approximately 80 to 90 percent of individuals with acute viral hepatitis and in 20 to 70 percent of those with cirrhosis. The test is also useful in the differential diagnosis of the two main types of jaundice. Today, thymol turbidity is rarely used. Techniques that are capable of distinguishing between the different types of globulins and other blood proteins are used instead. [See generally https://www.britannica.com/science/thymol-turbidity].

(2) Blood pressure—Blood pressure is a measurement of the force of blood against the arterial walls when the heart pumps. The pressure is measured in millimeters of mercury (mmHg) and is expressed as two numbers. For example, the optimal BP for an adult is 120 over 80, or 120/80. The top number, called the systolic pressure, measures the highest pressure exerted when the heart contracts. The bottom number, called the diastolic pressure, shows the minimum pressure against the arteries when the heart rests between beats. Blood pressure is measured with an instrument called a sphygmomanometer. It is measured with a cuff and stethoscope while the arm is in a resting position. The cuff is placed about one inch above the bend of the elbow, and is inflated until the mercury dial reaches 30 points higher than the person's usual systolic pressure, or 210 if previous data is not available. A stethoscope is placed on an artery in the inside of the elbow, and the air is slowly allowed to escape from the cuff. The point at which the sound of the pulse is first heard is the systolic pressure number; the point at which the sound disappears is the diastolic number. Several factors can affect blood pressure, so one high reading does not necessarily mean that a person has hypertension, or high blood pressure. Immediate stimuli such as fear, pain, anger, and some medications can temporarily raise a person's BP. Blood pressure readings can also be affected by factors such as, without limitation, (i) smoking, (ii) coffee or other caffeinated drinks, (iii) a full bladder, and (iv) recent physical activity. Blood pressure is also affected by one's emotional state and the time of day.

If a high reading has occurred, and one of these factors is present, then the person needs to be monitored repeatedly over a period of time to determine if this is a persistent Condition, or if the reading was simply based on circumstances.

Hence, an alternate type of Subject data input (and processing and output review), such as Subject eye data input, processing, and output as described by the invention, can potentially assist in measuring if a Subject's potential condition indication is more or less valid as well as its apparent trend.

(3) Pulse Oximetry—Pulse oximetry measures the oxygen level (oxygen saturation) in the blood. A pulse oximeter is a simple device that is used to measure how well oxygen is being sent from the heart to different parts of the body, including your legs, arms, among other parts. Every organ and system in your body needs a good supply of oxygen to survive and thrive. Without a proper amount of oxygen, cells will slowly start to malfunction and ultimately die. This can eventually lead to system and organ failure. [See generally https://www.besthealthncare.com/how-to-read-a-finger-pulse-oximeter/]. Conditions that may prevent one's lungs from inhaling sufficient oxygen include, without limitation, heart disease, anemia, collapsed lung, pulmonary embolism, and/or Covid 19. [Id.] Pulse oximetry may be used: (i) to monitor how well lung medicines are working, (ii) if you are suffering from conditions such as heart failure, heart attack, asthma, pneumonia, anemia, lung cancer, and chronic obstructive pulmonary disease, (iii) during or after a procedure that uses sedation, and (iv) to check whether you need a ventilator to help with breathing, and (v) to check if you have a moment when breathing stops while you are asleep. [Id.] Today pulse oximetry data can be obtained on an Apple Watch or similar device (and arguably the Subject owns this data) or on comparatively inexpensive standalone pulse oximeters which can be purchased on the internet. Hence, a Subject's pulse oximetry data can today be obtained directly by the Subject, as well as with the assistance of a Professional.

(4) Body Mass Index—Body mass index (BMI) is a measure of body fat based on height and weight that applies to adult men and women. [See generally https://www.nhlbi.nih.gov/health/educational/lose_wt/BMI/bmicalc.htm]. Your BMI is a good indicator of your risk factors for certain conditions like cardiovascular disease and diabetes. [See generally https://www.healthcentral.com/article/home-body-weight-tests]. Today smart scales make it easier than ever to measure user weight and usually contain a BMI measurement function to test a user's body fat percentage at home. For example, the Fitbit Aria WiFi Smart Scale measures a user's weight, body fat percentage, and BMI to provide a full picture of the user's weight management trends. These scales transmit an electrical signal from your feet and scan your body, and use WiFi to automatically transmit a user's weight and BMI data wirelessly to his or her smartphone or computer, and create for him or her a customized weight and/or BMI "data chart" showing trends based on the date of the weight and BMI measurement data points over time.

(5) Weight—"Underweight", "normal", "overweight", and "obese" are all labels for ranges of weight. Obese and overweight mean that your weight is greater than it should be for your health. Underweight means that it is lower than it should be for your health. Your healthy body weight depends on your sex and height. For children, it also depends on your age. A sudden, unexpected change in weight can be a sign of a medical problem. Causes for sudden weight loss can include, without limitation: (i) thyroid problems, (ii) cancer, (iii) infectious diseases, (iv) digestive diseases, (v) certain medicines. Sudden weight gain can be due to medicines, thyroid problems, heart failure, and kidney disease. See the discussion of smart scales under "Body Mass Index" above.

(6) Urine Sample Data—Clinical urine tests (also known as urinalysis, UA) is an examination of urine for certain physical properties, solutes, cells, casts, crystals, organisms, or particulate matter, and mainly serves for medical diagnosis. Urine culture (a microbiological culture of urine) and urine electrolyte levels are part of urinalysis. [See generally https://en.wikipedia.org/wiki/Clinical_urine_tests]. Many disorders may be detected in their early stages by identifying substances that are not normally present in the urine and/or by measuring abnormal levels of certain substances. Some examples include glucose, protein, bilirubin, red blood cells, white blood cells, crystals, and bacteria. They may be present because, without limitation: (i) there is an elevated level of the substance in the blood and the body responds by trying to eliminate the excess in the urine, (ii) kidney disease is present, or (iii) there is a urinary tract infection present, as in the case of bacteria and white blood cells. [See generally https://labtestsonline.org/tests/urinalysis #:~: text=A %20urinalysis %20is %20a %20group%20of %20physical %2C %20chemical %2C, and %20abnormal %20metabolism %2C %20cells %2C %20cellular %20fragments %2C %20and %20bacteria].

(7) Stool Sample Data—A stool test is used to detect the presence of blood or other gastrointestinal abnormalities, such as colon or gastric cancer, inflammatory bowel disease, hemorrhoids, anal fissures or infections. There are two main types of stool tests to choose from: (i) a fecal occult blood test (FOBT), which detects the presence of blood in your feces, and (ii) a stool DNA test, which detects the presence of genetic material from polyps and cancerous tumors. [See generally https://www.verywellhealth.com/stool-test-options-796641].

(8) Pregnancy Test Data—Human pregnancy tests work by checking a subject's urine (pee) for a hormone called human chorionic gonadotropin (HCG). A subject's body only makes this hormone if the subject is pregnant. Pregnancy tests are usually inexpensive—they can cost as little as a dollar. Sometimes you can get a free pregnancy test at certain health centers. You can also get a pregnancy test from your nurse or doctor, or community clinic. [See generally https://www.plannedparenthood.org/learn/pregnancy/pregnancy-tests].

(9) Saliva Test Data—A saliva test is a medical test in which a sample of saliva is analyzed, often in order to measure a person's hormone levels. Many saliva home test kits are available.

(10) Allergy Test Data—An allergy test is an exam performed by a trained allergy specialist to determine if the subject's body has an allergic reaction to a known substance. The exam can be in the form of a blood test, a skin test, or an elimination diet. Allergies occur when a subject's immune system, which is a subject's body's natural defense, overreacts to something in the subject's environment. For example, pollen, which is normally harmless, can cause a subject's body to overreact. Allergy tests involve exposing the subject to a very small amount of a particular allergen and recording the reaction. [See generally https://www.healthline.com/health/allergy-testing #allergy-types].

(11) ECG measurement and spot Atrial Fibrillation (AFib)—The irregular heartbeats of Atrial Fibrillation ("Afib") are not always medically dangerous, but they can lead to complications such as stroke, blood clots and even heart failure. Today ECG measurement and spot AFib can be obtained on an Apple Watch or similar device (and arguably the Subject owns this data) or on comparatively inexpensive standalone ECG measurement and spot AFib device. The Apple Watch can also occasionally check your heart rate with its automatic heart rate sensor, and will send you an alert if it notices anything abnormal. Hence, today a Subject's ECG measurement and spot AFib pulse oximetry data can be obtained directly by the Subject, as well as with the assistance of a Professional.

(12) DNA/Genetic Test Data—Currently, only about a quarter of cancer patients get detailed genetic testing of their tumors. [See generally A. Park, "Why doctors are turning to blood to learn more about tumors", Time, vol. 196, no. 15, 2020, at p. 25.]

(13) Brainwave Test Data—A brainwave is the rapid fluctuations of voltage between parts of the cerebral cortex that are detectable with, for example, an electroencephalograph (EEG), which allows researchers to note brain wave patterns. All humans display five different types of electrical patterns or brain waves across the cortex. Each brain wave has a purpose and helps serve us in optimal mental functioning. Data such as video or EEG measures taken over a period of time can be synchronized. This process can be used in diagnosing and monitoring epilepsy or monitoring shared behavioral and brain dynamics. [See generally https://itsusync.com/different-types-of-brain-waves-delta-theta-alpha-beta-gamma-ezp-9]. The detection of brain signals is achieved through electrodes placed on the scalp. There are several ways to develop a noninvasive brain-computer interface, such as EEG (electroencephalography), MEG (magnetoencephalography), or MRT (magnetic resonance tomography). [See generally https://search.yahoo.com/yhs/search;_ylt=AwrWmjlgRYNfYSsAQAYPxQt.;_ylu=Y29sbwNnc TEEcG9zAzEEdnRpZAMEc2VjA3BhZ2luYXRpb24-?p=brainwave+data+definition&ei=UTF-8&type=em_appfocus1_me&fr=yhs-pty-pty_email&fr2=rs-bottom %2Cp %3As %2Cv %3Aw %2Cm %3Aats¶m1=20190209&param2=0671e462-beec-4071-b2dc-f32f8950ee2a&param3=email_%7EUS %7Eapp focus 1%7E¶m4=g-ccc1-lp0-bb8-sbe-ab %7EEdg eium %7Ebrainwave+data %7ED41D8CD98F00B2 04E9800998ECF842 7E %7EWin10&hsimp=yhs-pty_email&hspart=pty&b=11&pz=10&bct=0&xargs=0].

(14) Glucose Monitoring Device Data—A glucose monitoring device is a device worn by a person who is a diabetic, which provides continuous glucose monitoring for the management of diabetes. It detects trends and tracks patterns aiding in the detection of episodes of hyperglycemia and hypoglycemia, thereby facilitating both acute and long-term therapy adjustments. An example of such a device is the "Freestyle Libre 14 day Flash Glucose Monitoring System", a product of Abbott Diabetes Care, Inc. Also, a California-based company, Dexcom, in 2019 announced that its G6 glucose tracker would soon be able to send monitoring data to the Apple Watch, benefiting Apple Watch users with diabetes.

(15) "Brain Age Index" Data—Researchers recording polysomnograms—records of brain waves, blood oxygen levels, heart rates, respiration, and muscle movements during sleep—have created a "brain age index" derived from a machine learning algorithm that analyzes brain waves during different stages of sleep and models normal brain activity across the human lifespan. The brain age index is basically the brain age subtracted by the chronological age. A high brain age index is a strong indicator of accelerated aging. Patients with dementia tend to have brain activity that appears "older" than the patient's chronological age. It is the inventor's view that the brain age index—in combination with other screening tools, such as the collection, analysis, and cross-comparison of eye data, as described in, and part of, the invention—can act as an "early warning system" for dementia and other neurological conditions. In 2014, an estimated five million adults over the age of 65 suffered from dementia, and that number is projected to reach nearly 14 million by 2060. A recent study suggests 61.7 percent of dementia cases go undiagnosed. [See generally https://www.thecrimson.com/article/2020/10/9/dementia-prediction-tool/]

(16) Prescription Pharmaceuticals, Nutraceuticals, and other Over-the-Counter Drugs being Consumed by the Subject (and Data Related Thereto)—

A prescription drug (also prescription medication or prescription medicine) is a pharmaceutical drug that legally requires a medical prescription to be dispensed. In contrast, over-the-counter drugs can be obtained without a prescription. The reason for this difference in substance control is the potential scope of misuse, from drug abuse to practicing medicine without a license and without sufficient education. Different jurisdictions have different definitions of what constitutes a prescription drug. [See generally https://en.wikipedia.org/wiki/Prescription_drug #:~: text=A %20prescription %20dru g %20%28also %20prescription %20medication %20or %20prescription,over-the-counter %20drugs %20can %20be %20obtained %20without %20a %20prescription]. A nutraceutical or 'biocuetical' is a pharmaceutical alternative which claims physiological benefits. In the United States, "nutraceuticals" are largely unregulated, as they exist in the same category as dietary supplements and food additives by the FDA, under the authority of the Federal Food, Drug, and Cosmetic Act. The terms "nutraceutical" and 'biocuetical' are not defined by U.S. law. Depending on its ingredients and the claims with which it is marketed, a product is regulated as a drug, dietary supplement, food ingredient, or food. [See generally https://en.wikipedia.org/wiki/Nutraceutical].

Prescription drugs, nutraceuticals, and over-the-counter (OTC) drugs can have side effects. Side effects, also known as adverse events, are unwanted or unexpected events or reactions to a drug. Side effects can vary from minor problems like a runny nose to life-threatening events, such as an increased risk of a heart attack. Several things can affect who does and does not have a side effect when taking a drug—age, gender, allergies, how the body absorbs the drug, other drugs, vitamins, and dietary supplements that you may be taking. [See generally https://www.fda.gov/drugs/drug-information-consumers/finding-and-learning-about-side-effects-adverse-reactions].

It should be noted that the invention in measuring and processing Subject's eye data (as described in the invention) has the potential to measure some of the effects on the eyes, body and/or brain of prescription drugs, nutraceuticals, and over-the-counter drugs on the user (human or animal) who or which are using them. For example, but without limitation, as earlier noted in 0005, "taking a common, over-the-counter medicine can cause fluctuations in your vision that might make a difference in your exam."

This attribute of the invention—i.e., the potential to measure some of the effects on the eyes, body and/or brain of prescription drugs, nutraceuticals, and over-the-counter drugs on the user (human or animal) who or which are using them—is important on a number of levels, including the fact that until the world produces customized prescription drugs, nutraceuticals, and over-the-counter drugs in customized doses based on a user's blood type, DNA, weight, gender, et al., such "additives" to the user's body will affect different users differently, and those differences in response are important to understand (in part because it allows for potentially better identifying and facilitating both acute and long-term therapy adjustments for user).

Summary Overview re Adding Additional "Health Data". Hence, adding an alternate type of Subject "health data" to a Subject's eye data (as described by the invention), can potentially assist in measuring if a Subject's potential Condition indication is either more or less valid as well as its apparent trend and the speed of that trend (thereby potentially better facilitating both acute and long-term therapy adjustments).

Over time, comparing and cross-referencing alternative types of Subject "health data" together with the Subject's eye data (as described by the invention) can potentially result in a virtuous cycle which potentially strengthens and cross-validates the potential Subject Condition indications identified by each type of data.

While any type of Subject "health data" can potentially come first in identifying a potential Subject Condition indication, which if potentially identified may be followed by the addition of one or more other types of "health data" for greater or lesser potential cross-validation, it is the inventor's view that the invention, given its ability in certain modes of use to work in an automatic mode or semi-automatic mode requiring little if any effort by the Subject, may for many potential Subject Conditions be the first line of potential indication of a Subject Condition, identifying Subject Conditions that otherwise might never be addressed or otherwise might be addressed much later, at a time in which it is much more costly and difficult to address the Condition, if at that point the Condition can be meaningfully be addressed at all.

D. Eye Exam/Eye Monitoring Output (For Healthcare Professional or Computer Vision)

Examples of alternative potential invention data outputs include, without limitation:

(i) a voice report (by AI-powered chatbot, Professional, or otherwise).

(ii) a written online report.

(iii) a computer monitor/screen with a still or video image and/or display with words and/or voice (by AI-powered chatbot, Professional, or otherwise).

(iv) an augmented reality still or video image and/or display with words (on or through, for example, AR output headsets, glasses, and/or goggles, AR contact lenses, AR projector, and/or a device that can display an AR "projection", such as, without limitation, a smartphone or smart pad) (with each still or video image being in 2D or 3D or 4D [i.e., time lapse] in black and white/grayscale, real color, and/or assigned colors for emphasis), to the extent the camera output is in the form of real-world visual Eye data (but including data from thermal cameras, and other sensors, et al.).

Note: Thermal infrared cameras and electrooculography (i.e., the measurement of the electrical potential between electrodes placed at points close to the eye), for example, will not render real-world images as other cameras in other invention input devices do. Still their data output can be displayed on output devices and configured in a number of ways.

(v) a virtual reality still or video image and/or display with words (with each still or video image being in 2D or 3D or 4D [i.e., time lapse] in real color, assigned colors, or black and white/grayscale), to the extent the camera output is in the form of real-world visual Eye data.

Note: Thermal infrared cameras and electrooculography (i.e., the measurement of the electrical potential between electrodes placed at points close to the eye), for example, will not render real-world images as other cameras in other invention input devices do. Still their data output can be displayed on output devices.

(vi) a 3D printer, in real color, assigned colors, or black and white/grayscale.]

Note: The invention software can employ "markers" (solid bright colors may be best) to visually identify in invention output the indication that has been identified as a potential Subject Condition.

1. Computer Screen and Projectors.

a. Computer Screens/Monitors. The output computer screens/monitors used by the invention for Professionals are the same as or similar to commercially available high-resolution, high refresh-rate, high response time, high color gamut, and high contrast computer and television video screens/monitors today, and those that have been developed but have not yet been released into the commercial marketplace.

For example, without limitation mini LED panels and OLED, each which produce their own light source and are more stable, are but two technologies improving video display performance.

The invention provides the user with touch screen capability, including the potential ability to touch the screen and increase-or-decrease the size of the image on the screen, or to do so through software and a mouse/trackpad/finger or similar control input device, change the resolution of the screen and/or visually increase-or-decrease the size of the image on the screen, etc.

The output computer screens/monitor ideally (but not necessarily) will be 3D capable.

The output computer screen/monitor or computer to which it is connected will have a "speaker/headphone/earphone" and microphone so the user can hear audio data from the computer (e.g., the computer's AI-powered chatbot, the Subject's voice, et al.) and speak commands to the computer and/or make comments to the Subject [similar to speaking to Amazon's Alexa]).

b. Projectors. Output computer projectors used by the invention will have high resolution, probably (but not necessarily) show 3D images, have excellent color accuracy, have appropriate brightness, and other appropriate qualities known to those skilled in the art.

The computer to which the projector is connected will have a "speaker/headphone/earphone" and microphone so the user can hear audio data from the computer (e.g., the computer's AI-powered chatbot, the Subject's voice, et al.) and so the Professional can speak commands to the computer and/or make comments to the Subject [similar to speaking to Amazon's Alexa]).

2. AR/VR Output Glasses and/Goggles and/or Headsets.

a. AR Output Glasses—The AR output glasses (the "AR Output Glasses") are similar to the Special Input Glasses (described above), but are intended as an output device and not an input device. Information is displayed in both lenses.

The AR Output Glasses will function as mobile (but wirelessly connected to a smartphone or its equivalent or a PC or larger computer), tethered (connected by wire to a PC or larger computer), or standalone (functioning and communicating totally on its own).

In addition, the AR Output Glasses will have a "speaker/headphone/earphone" and microphone (which may-or-may not use the functionality of the smartphone or its equivalent [as a headphone wirelessly or by wire connected to a smartphone does today], depending on the type of AR Output Glasses being used), so the wearer can hear audio data from the computer (its AI-powered chatbot, the Subject's voice, et al.) and can speak commands to the computer and/or make comments to the Subject [similar to speaking to Amazon's Alexa]).

The output AR Out Glasses will allow authorized Professionals to, by manual control, verbal input to, online selections, or otherwise, for example but without limitation:

(i) focus in-or-out or increase-or-decrease the magnification of the image or video being displayed, as well as increase-or-decrease the speed of the video being displayed (i.e., time lapse imagery).

(ii) project a "split screen" display, to, without limitation:
  (x) compare a Subject's eye or specified Eye data at an earlier date to the same Subject's eye or specified Eye data at a later date, or
  (y) compare a Subject's eye or specified Eye data at a certain date to a "healthy eye" or "healthy specified Eye data", with appropriate adjustments made for age, et al.

b. AR Output Goggles—The AR output goggles ("AR Output Goggles") are similar to the input Special Input Goggles (described above), but are an output device and not an input device. Information is displayed in both lenses.

The AR Output Goggles will function as mobile (but wirelessly connected to a smartphone or its equivalent or a PC or larger computer), tethered (connected by wire to a PC or larger computer), or standalone (functioning and communicating totally on its own).

Note: In some mobile AR Output Goggles there is a slot into which the user places his or her smartphone or its equivalent.

In addition, the AR Output Goggles will have a "speaker/headphone/earphone" and microphone (which may-or-may not use the functionality of the smartphone or its equivalent [as a headphone wirelessly or by wire connected to a smartphone does today], depending on the type of AR Output Goggles are being used), so the wearer can hear audio data from the computer (its AI-powered chatbot, the Subject, et al.) and speak commands to the computer or the Subject (similar to speaking to Amazon's Alexa).

The AR Output Goggles will allow authorized Professionals to, by manual control, verbal input to, online selections, or otherwise, for example but without limitation:

(i) focus in-or-out or increase-or-decrease the magnification of the image or video being displayed, as well as increase-or-decrease the speed of the video being displayed (i.e., time lapse imagery).

(ii) project a "split screen" display, to, without limitation:
  (x) compare a Subject's eye or specified Eye data at an earlier date to the same Subject's eye or specified Eye data at a later date, or
  (y) compare a Subject's eye or specified Eye data at a certain date to a "healthy eye" or "healthy specified Eye data", with appropriate adjustments made for age, et al.

c. VR Headsets, Goggles, and Glasses—

The terms "VR headsets", "VR goggles", and "VR glasses", are used interchangeably with no difference between them and hereafter will be collective known as "VR Output Headsets".

The VR Output Headsets are similar to virtual reality headsets known to those skilled in the art, but are a part of the overall instant invention with a specific usage as described herein.

The VR Output Headset will function as:
(i) mobile (but wirelessly connected to a smartphone or its equivalent or a PC or larger computer),
(ii) tethered (connected by wire to a PC or larger computer), and/or
(iii) standalone (functioning and communicating totally on its own).

Note: In some mobile VR Output Headsets there is a slot into which the user places his or her smartphone or its equivalent.

The output VR Output Headsets will have a "speaker/headphone/earphone" and microphone (which may-or-may not use the functionality of the smartphone or its equivalent [as a headphone wirelessly or by wire connected to a smartphone does today], depending on the type of VR Output Headset is being used), so the wearer can hear audio data from the computer [its AI-powered chatbot, the Subject's voice, et al.] and speak commands to the computer or provide comments to the Subject [similar to speaking to Amazon's Alexa]).

The VR Output Headset will allow authorized Professionals to, by manual control, verbal input to, online selections, or otherwise, for example but without limitation:
  (i) focus in-or-out or increase-or-decrease the magnification of the image or video being displayed, as well as increase-or-decrease the speed of the video being displayed (i.e., time lapse imagery).
  (ii) project a "split screen" display, to, without limitation:
    (x) compare a Subject's eye or specified Eye data at an earlier date to the same Subject's eye or specified Eye data at a later date, or
    (y) compare a Subject's eye or specified Eye data at a certain date to a "healthy eye" or "healthy specified Eye data", with appropriate adjustments made for age, et al. Controls to allow for focusing in or magnifying of the image or video being displayed. Controls to allow for the slowing of speed of video being displayed.
  3. AR Contact Lenses. AR contact lenses ("AR Invention Output Contact Lenses") solely for reviewing the invention output may be a type of invention output used by Professionals and/or others.

AR Invention Output Contact Lenses would be custom-made to fit the wearer, would be wireless, and can be connected to a computer/smartphone and/or similar device with a WiFi relay, with a data exchange transmission protocol embedded inside each of the contact lenses with a data exchange rate in a 4G or 5G format. They would be powered, without limitation, by a micro-battery (e.g., without limitation, a stretchable self-healing Li-ion micro-battery, or a thin-film solid-state battery) within each contact lens.

Micro-components (including for example, without limitation, an ARM-based processor, a communications chip, and an imaging sensors will provide complex computing functions) and micro-displays are integrated directly into each autonomous contact lens. The lenses will be compliant with ocular safety norms, such as EN62471-2008 and its progeny.

The lens will rely on an internet connection provided by a smartphone or its equivalent or some other device for sending and receiving data.

Information with respect to AR contact lenses such as the AR Invention Output Contact Lenses is known to those skilled in the art.

The AR Invention Output Contact Lenses can work together with a "speaker/headphone/earphone/earplug" and microphone (which may-or-may not use the functionality of the smartphone or its equivalent [as a headphone wirelessly or by wire connected to a smartphone does today], so the wearer can hear audio data from the computer [its AI-powered chatbot, the Subject's voice, et al.] and speak commands to the computer or provide comments to the Subject [similar to speaking to Amazon's Alexa]).
  4. AR Projectors. AR projectors solely for reviewing invention output ("AR Invention Output Projectors") can be a type of invention output used by Professionals and/or others.

AR projectors such as the LF2 are already being sold in the commercial marketplace.

Yinscorp Ltd. has its Count Projector, which transforms a smartphone into an interactive augmented reality projector.

Information with respect to AR projectors is known to those skilled in the art.

The AR Invention Output Projector can work together with a "speaker/headphone/earphone/earplug" and microphone (which may-or-may not use the functionality of the smartphone or its equivalent [as a headphone wirelessly or by wire connected to a smartphone does today], so the wearer can hear audio data from the computer [its AI-powered chatbot, the Subject's voice, et al.] and speak commands to the computer or provide comments to the Subject [similar to speaking to Amazon's Alexa]).
  5. AR Projections from, without limitation, a Smartphone, Smart Pad, or their Equivalents. AR projections from, without limitation, a smartphone, smart pad, or their equivalents ("Invention AR Projections on a Smartphone et al.") can be a type of invention output used by Professionals and/or others.

Yinscorp Ltd. has its Count Projector, which transforms a smartphone into an interactive augmented reality projector.

Smartphones themselves or their equivalents can generate AI projections, although commercial versions have yet to be released.

Information with respect to AR projections from, without limitation, a smartphone, smart pad, or their equivalents, is known to those skilled in the art.
  6. 3D Printer Output. A 3D printer is a computer-aided manufacturing (CAM) device that creates three-dimensional objects. Like a traditional printer, a 3D printer receives digital data from a computer as input. However, instead of printing the output on paper, a 3D printer builds a three-dimensional model out of a custom material.
    3D printer output ("Invention 3D Printer Output") can be a type of invention output used by Professionals and/or others. 3D printer output may assist in the visualization in a material 3D format of a potential Subject's eyes Condition.
    Note: The output, in whatever custom material, could be in real color, assigned colors, or black and white/grayscale.
    Information with respect to this type of output is known to those skilled in the art.

It should be noted that a Professional or others may view invention output through any combination or permutation of the above-mention invention output devices.
  E. Eye Exam/Eye Monitoring Output (For Subject Whose Eyes Are Being Examined or Monitored [or if the Subject is an Animal its Owner]).

Some of the invention output intended for Professionals may be useful for a Subject to directly see or hear to better understand a potential Condition they may have, and to motivate them in certain circumstances to act to alleviate the potential Condition.

For example, it may be useful for a Subject to be able to directly see certain Professional-selected invention output for certain potential Conditions:
  a. Computer Screen/Monitor. If the Subject owns an appropriate computer screen or monitor (or can borrow or lease one), the invention output can be digitally transmitted to the Subject for review and discussion with the Subject (by AI-powered chatbot, a Professional, or otherwise).
  b. Projector. If the Subject owns an appropriate projector (or can borrow or lease one), the invention output can be digitally transmitted to the Subject for review and discussion with the Subject (by AI-powered chatbot, a Professional, or otherwise).
  c. AR Output Glasses or AR Output Goggles. If the Subject owns appropriate AR Output Glasses or AR Output Goggles (or can borrow or lease one), the invention output can be digitally transmitted to the Subject for review and discussion with the Subject (by AI-powered chatbot, a Professional, or otherwise).
  d. VR Output Headset. If the Subject owns an appropriate VR Output Headset (or can borrow or lease one), the invention output can be digitally transmitted to the Subject for review and discussion with the Subject (by AI-powered chatbot, a Professional, or otherwise).
  e. AR Invention Output Contact Lenses. If AR Invention Output Contact Lenses become commonplace and the Subject already owns a pair of such AR lenses or their equivalent (given that such lenses are custom-made), the invention output can be digitally transmitted to the Subject for review and discussion with the Subject (by AI-powered chatbot, a Professional, or otherwise).
  f. AR Invention Output Projector. If AR Invention Output Projectors become commonplace and the Subject owns one or its equivalent (or can borrow or lease one), the invention output can be digitally transmitted to the Subject for review and discussion with the Subject (by AI-powered chatbot, a Professional, or otherwise).
  g. Invention AR Projections on a Smartphone et al. The Subject will most likely own (or can borrow or lease) one of these invention output devices (i.e., a smartphone or smart pad with this AR capability), and the invention output can be digitally transmitted to the Subject for review and discussion with the Subject, by AI-powered chatbot, a Professional, or otherwise).
  h. Invention 3D Printer Output (which invention output can be physically delivered to a Subject for review and discussion with the Subject, by AI-powered chatbot, a Professional, or otherwise).
F. Software—Both "If-Then" and "Predictive". Every task has a group of decisions at its heart, and those decisions have some predictive element.
  1. "If-Then" Software. Use software with basic "if-then" rule-based logical intelligence.

For some decisions, you can articulate the requisite judgment and express it as computer code. We often, for example, explain our thinking to other people. Codifiable judgment allows you to fill in the part after "then" in the "if-then" statements. When this happens judgments can be enshrined and programmed.

In some cases, the number of possible predictions may make it too costly for any human to judge all the possible payoffs in advance. Instead, a human needs to wait for the prediction to arrive and then assess the payoff, which is close to how most decision-making currently works, whether or not it includes machine-generated predictions.

The downside of "if-then" software is sometimes there are too many "ifs" to possibly code. Neither traditional statistical methods nor algorithms of if-then statements tend to operate well in complex environments.

For example, autonomous vehicles, which have existed in controlled environments for over two decades (generally limited to places with detailed floor plans, such as warehouses and factories), could not function outside highly predictable, controlled environments until engineers reframed navigation as a predictive problem. Instead of telling the machine what to do in each circumstance, engineers focused on a single predictive problem: What would a human do?

2. "Predictive" Software. Artificial intelligence (AI) is predictive technology. Predictions are inputs to decision-making. AI arguably improves prediction and drops its cost. It can work together with and as part of the workings of digital cameras, machine/computer vision, video and/or audio (known as "natural language processing"), and, of course, much more.

One type of AI, known as "deep learning", relies on an approach called "back-propagation". It "learns" through example.

Machines and humans have strengths and weaknesses in the context of prediction. Prediction machines are better than humans at factoring complex situations among different indicators, especially in situations with rich data. Humans, however, have cognitive models of how the world works (causality versus correlation), and typically do better than predictive machines in settings with "thin data" and "human prediction by exception".

The unit cost per prediction falls as the frequency increases. Human prediction does not scale the same way.

Prediction machines are valuable in part because prediction is a key ingredient in decision-making under uncertainty. Prediction machines can reduce uncertainty, but will not always eliminate it. AI can increase confidence, and in the case of the invention indicate to the person whose eyes are being examined that an issue has been indicated, and that they may want to inform a medical professional of the indication and have the medical professional decide what to do or not do. The appropriate medical professional can decide what is driving the conclusion and make the ultimate diagnosis.

Note: A prediction is not a decision, but only a component of a decision. The other components are judgment, action, and outcome, compared to three types of data, those being input, training, and feedback.

For the invention, AI can provide the probabilities, but for now human experts will translate the AI output and actual diagnostic and decide treatment.
  (i) Supervised learning. Supervised learning is a technique used when you have a good idea of what you want to predict.
  (ii) Reinforcement learning. Reinforcement learning, in contrast to supervised learning, is a technique used when you do not have good data, but you can tell, after the fact, how right you were.

While training the prediction machine most likely happens in the cloud, once the machine is trained it may be possible to do predictions directly in the device without sending the data back to the cloud.

In addition, while this application describes in various locations carrying out and storing certain operations in the "cloud" it should be understood that any form of distributed computing or storage could be used, including but not limited to EDGE AI and EDGE computing
  3. Geometric Deep Learning. Geometric deep learning is an emerging subfield of AI that can learn patterns on curved surfaces. It can be used for, among other things, to detect potential interactions among proteins the complex folded molecules responsible for many biological processes—40,000 times faster than conventional methods. It allows researchers to scan a protein's 2D surface for what researchers call interaction fingerprints: features learned by a neural network that indicate another protein could bind there, allowing for predicting protein interactions. It is the inventor's view that geometric deep learning as part of the invention software will prove extremely useful for detecting patterns in data gathered from the Subject's eyes and greatly enhance the predictive ability of the invention for Subject Conditions. An embodiment defines using Geometric deep learning techniques and their progeny as part of the eye monitoring and analysis and as part of the invention.

4. Gauge CNN Algorithms. It is the inventor's view that Gauge CNN algorithms and their progeny will prove extremely useful for detecting patterns in data gathered from the irregularly curved surfaces of Subject's eyes, eye lids, et al. It is also the inventor's view that Gauge CNN and its progeny will be much more efficient in the use of training data.

Please note that Qualcomm is now working on improved computer vision applications based on Gauge CNNs.

An embodiment defines using Gauge CNN techniques and their progeny as part of the eye monitoring and analysis and as part of the invention.

[https://www.quantamagazine.org/an-idea-from-physics-helps-ai-see-in-higher-dimensions-20200109/]

Eye Monitoring Service: Software Architecture

The software components included in one embodiment of the eye-monitoring service are depicted in the figure above.

First, this embodiment of the invention includes a Patient Mobile App that runs on a user's handheld computing device such as a smartphone or small tablet. The Patient Mobile App may be acquired from an online app marketplace, such as the Apple App Store or Google Play. The Patient Mobile App includes several subcomponents. A user interface subcomponent implements the menus, graphics, buttons, and data displays with which a user interacts when the Patient Mobile App is active. An image/video capture subcomponent implements logic for initializing the device camera, configuring the camera's settings to increase captured image quality, capturing raw images, and storing images to the flash memory of the mobile device. A user data component is responsible for storing information about the current patient user, such as the unique identifiers that associate the user with medical records and provider information that are stored securely within the server-side applications and databases of the eye-monitoring service.

Using the Patient Mobile App, a patient can enroll or register in the eye-monitoring service. Optionally, the eye-monitoring service may be configured to restrict enrollment to patients who have been invited by a medical provider. A user who has successfully enrolled in the service is able to log in to the Patient Mobile App using standard means, such as a password, fingerprint, or facial recognition. Once logged in, a patient can view a variety of data that has been collected, stored, or generated by the eye-monitoring service. For example, a patient can view images and videos that have been collected using the Patient Mobile App. Similarly, a patient can view past and current alerts and notifications generated by the eye-monitoring service. A patient can also review messages sent to or received from the patient's medical provider. A patient can also initiate new correspondence with his or her medical provider. Depending on the configuration of the eye-monitoring service, a patient may also be able to initiate the capture of a new eye image or video. Also depending on the configuration of the eye-monitoring service, a patient may be able to view health metrics and evaluations generated by the eye-monitoring service.

Second, this embodiment of the invention includes a Medical Professional Portal that may be accessed through a web browser or mobile app. For example, a medical professional may opt to access the Medical Professional Portal through a web browser when in an office setting that includes desktop and laptop computers, and the medical professional may opt to access the Medical Professional Portal through a mobile app at other times and locations.

Using the Medical Professional Portal, a medical professional may, for example, view a list of patients whose medical information the medical professional is authorized to view. The medical professional may view records associated with these patients, such as the patient's demographic and medical information as well as images and videos the patient's eyes that have been captured by the eye-monitoring system. The medical professional may also view current and past alerts that have been generated by the eye-monitoring system. The medical professional may also view the results of automated analyses and assessments performed by the eye-monitoring system. For example, the medical professional may view in a table, graph, or other format the changes that have occurred to the patient's eyes over a period of time. The medical professional may similarly view risk metrics and scores produced by the eye-monitoring system.

Both the Patient Mobile App and the Medical Professional Portal are connected via an Internet connection to a collection of Eye-Monitoring Server Applications that run on server computers. The Patient Mobile App and Medical Professional Portal exchange a variety of information with the Eye-Monitoring Server Applications using an encrypted, secure data transmission protocol, such as HTTPS. For example, when a new patient user registers for the service or changes information in his or her profile, including medical information, the Patient Mobile App uploads the patient information to the Eye-Monitoring Server Applications where it is added or updated within a secure data storage system. As another example, when a new image or video has been captured by the Patient Mobile App, the Patient Mobile App uploads the image(s) and video(s) to the Eye-Monitoring Server Applications. Similarly, when a medical professional selects to view a patient's information or eye images or videos using the Medical Professional Portal, the information is securely downloaded from the Eye-Monitoring Server Applications to the Medical Professional Portal.

The Eye-Monitoring Server Applications include applications and programs for processing and analyzing eye images and videos in a variety of ways. One server application performs pre-processing of raw images and videos received from the Patient Mobile App. This application reads metadata associated within the image or video, including the video format, resolution, creation time, patient name and ID, and so on, and inserts a record containing this information in a database.

Another server application processes the images and videos to assess their quality. This application analyzes the videos to determine the position of the eyes within the image or video and evaluate whether the lighting, color, clarity, and stability in the image or video are acceptable. This server application may also include the capability to improve the image or video in various ways. For example, this server application may crop out portions of the image or video that do not contain the eyes or are not otherwise useful. The server application may attempt to adjust image characteristics such as white balance. The server application may run a stabilization algorithm on a video to reduce shakiness and keep the position of the eyes in the video constant. When an image or video is received that does not pass the quality assessment, and the quality cannot be improved through the mechanisms described, the server application may generate an alert or notification that is transmitted to the Patient Mobile App advising the patient that the image or video was unusable and a new image or video should be captured.

Another server application implements algorithms for generating models and measurements of the patient's eye and eye parts. This server application may compute measurements of the size and shape of the eye, eyelid, iris, pupil, and/or retina. This server application may also characterize the color of the eye (e.g., redness or yellowness); the presence and position of blood vessels; or the presence of other anomalous structures. This server application may be configured to compute specific models and measurements for particular users and may be calibrated based on past images, videos, models, and measurements stored within the eye-monitoring service's databases.

Other server applications are responsible for performing diagnostic analyses. These diagnostic applications are configured to assess the risk or probability that a patient has a particular medical condition or the severity of a known medical condition has changed. One diagnostic application may be programmed to perform comparative analyses, in which images, videos, models, or measurements of a patient's eyes are compared with past images, videos, models, or measurements of the same patient, a known healthy patient, or a known diseased patient. Such an application may, for example, determine whether the patient's eyes have changed in shape or color or whether new anomalous structures have appeared.

Another diagnostic application may be programmed to use machine learning techniques to quantify the risk that a patient has a particular condition based on an image or video of the patient's eye. The machine-learning-based diagnostic application may be constructed using supervised learning techniques, in which a machine learning algorithm is supplied with training data to classify inputs. In the eye-monitoring service, a diagnostic application that uses supervised machine learning may use the images and videos collected by the Patient Mobile App, eye models and measurements computed from those images and videos, and medical and demographic information provided by the patient or medical provider to classify patients as high risk or low risk for a particular condition. The diagnostic application may also provide a probability distribution describing the risk of a particular patient for a particular condition. The training data needed by the supervised machine learning algorithm may be provided in the form of a dataset that has been collected external to the eye-monitoring service, but in the preferred embodiment the eye-monitoring service is able to use its own collected data as training data. For example, if the eye-monitoring service collects images of a patient's eyes and the subsequently the patient is diagnosed in a medical professional's office with a particular condition, this finding can be fed back into the eye-monitoring service as a data point for training the supervised machine learning algorithm.

The machine-learning-based diagnostic application may also be constructed using unsupervised machine learning techniques, which are helpful for finding undiscovered patterns in data. Unsupervised learning may be used to cluster patients into similar groups based on eye images, videos, models, measurements, demographic data, and medical history. This analysis may then indicate previously unknown patterns in the data or identify outliers that, along with the subject matter expertise of medical professionals, could be used to improve diagnoses of eye conditions or other conditions that affect the eye. For example, if the cluster analysis produces a cluster of patients among which the incidence of a condition is higher than normal, it may indicate that some characteristic of that group is associated with elevated risk for the condition.

The eye-monitoring service is designed as an extensible platform such that new data processing and diagnostic applications may be "plugged-in" over time. If medical researchers develop a new diagnostic engine for a particular disease based on image processing and machine learning techniques, that engine can be plugged-in to the eye-monitoring service through the use of standard interfaces and software adapters. For example, the eye-monitoring service may optionally be implemented using web services and protocols that allow for individual components and application to be inserted and removed from the system over time.

6. Local Device Software Upgrades/Over-the-Air Software Upgrades.

Tesla Analogy. In an effort to improve its autonomous driving software, Tesla collects driving data from each of its cars as they are driven by their owners, and uses artificial intelligence software and other means to process the data in a manner to potentially improve the company's autonomous driving software. Periodically, Tesla sends over-the-air software updates to cars it sold to their owners so the cars are able to perform better based on the data that Tesla collected and processed, to make its self-driving software (and other types of software in Tesla vehicles) perform better.

In a similar manner, in the cloud (or locally for Edge AI and edge computing), the Eye data of consenting Subjects will be processed using AI software and other means to process the data in a manner to potentially:
 (i) Improve the invention's Rules-based programs/"if-then" and/or predictive and other software capabilities, and
 (ii) Discover new correlations with respect to the eyes of Subject/users of the invention as they relate to potential diseases and Conditions of a Subject's eyes, body and/or brain (and vice versa).

Somewhat similar to the manner in which certain deep learning programs use back-propagation to improve the efficacy of the predictiveness of the program, the invention may ask follow-up questions of the user to refine the Rules-based programs/"if-then" and/or predictive aspect of what the invention is measuring.

Figure 5:
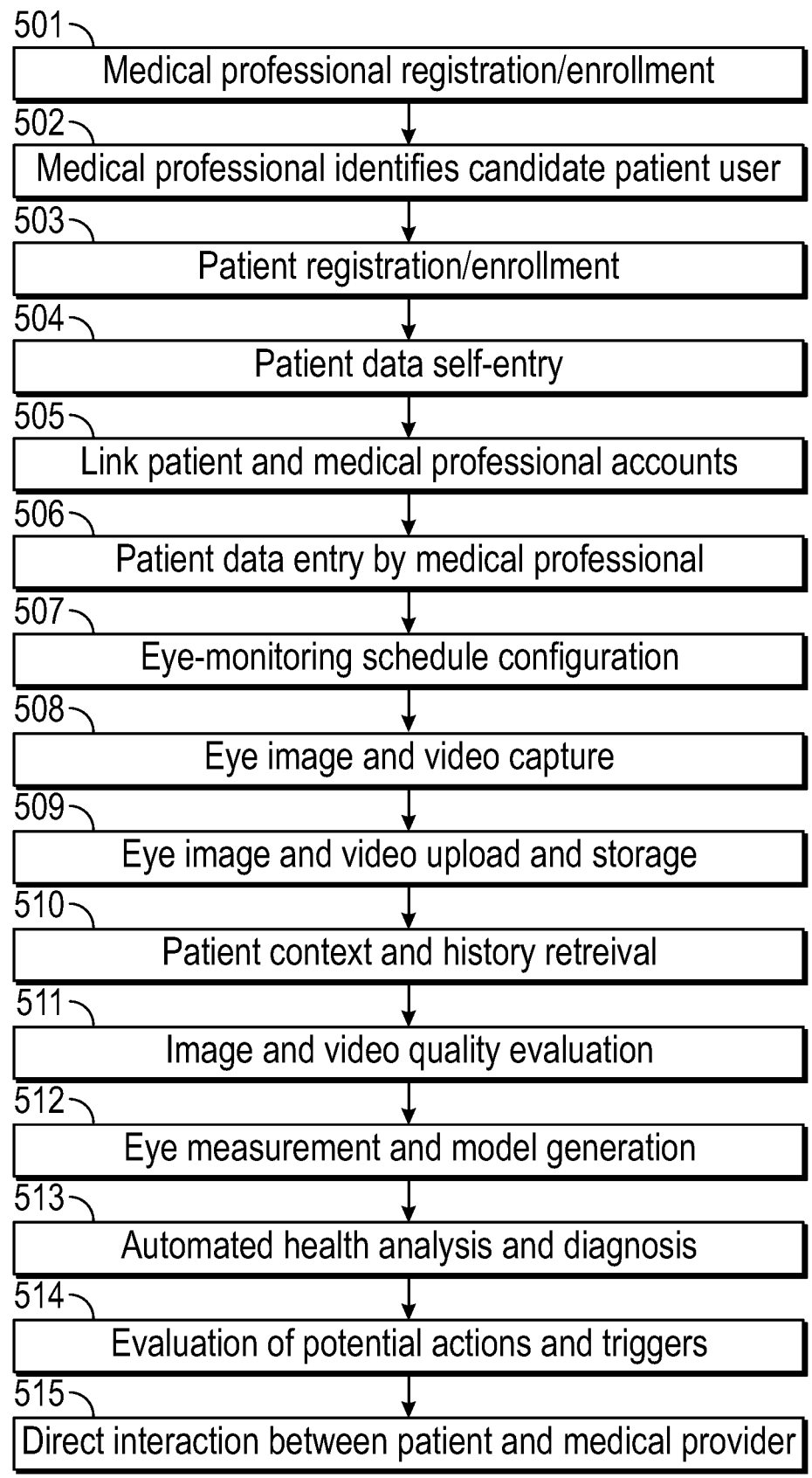
FIG. 5 shows a flowchart of operation.

The processors can run a flowchart, such as shown in FIG. 5. At 501, a Professional signs up to use the invention's app-based eye-monitoring service to monitor Subject/patients. The Professional receives training regarding the correct use of the service and is provided with user credentials to access the eye-monitoring service through a web browser or mobile app.

b. At 502, the Professional informs a Subject/patient that the Subject/patient has an elevated risk for a disease or Condition. The disease or Condition may be at least partially diagnosed through visual inspection of the eye or may include symptoms that appear in the eye, as explained fully elsewhere in this document. For example, the Subject/patient may be at high risk for jaundice, which may cause yellowish or greenish pigmentation of the whites of the Subject/patient's eyes. The Professional advises the Subject/patient that the Subject/patient is eligible to enroll in an app-based eye-monitoring service which may facilitate detection of the disease or Condition.

c. At 503, the Subject/patient elects to enroll in the app-based eye-monitoring service. The Subject/patient downloads and installs the mobile app from an online app marketplace, such as the Apple App Store or Google Play. The Subject/patient is prompted to hear and/or read and accept the necessary terms and conditions to use the service. The Subject/patient may be provided the option to view a video, audio, or text tutorial explaining how the service works, what information the service gathers, and how that information will be used.

d. At 504 the Subject/patient enters various information about himself or herself and his or her medical history. For example, the Subject/patient may preferably enter information including but not limited to her name, gender, age, height, weight, and medical provider. The Subject patient may also enter, or arrange for others to enter, Additional Information and/or Other Information.

e. At 505, a notification is sent to the Subject/patient's Professional advising the Professional that the Subject/patient has enrolled in the eye-monitoring service. The notification may be provided, without limitation, by phone, text message, email, or push notification. The Professional confirms that the Subject/patient is, in fact, a current Subject/patient of the Professional and is a candidate for the eye-monitoring service. The Subject/patient's user account and the Professional's user account become "linked" such that the Professional will receive further notifications regarding the Subject/patient's health, when appropriate, and view and edit the Subject/patient's medical data stored within the service.

f. At 506, the Professional inputs information regarding the Subject/patient's medical history and the disease or condition for which the patient may have an elevated risk. For example, the Professional may indicate that the Subject/patient has an elevated risk for jaundice.

g. In step 507, the eye-monitoring service is configured with an eye-monitoring schedule. The eye-monitoring schedule may be determined by the service itself (automatically in a "customized" manner by the service software or by a standard default) based on the information provided by the Subject/patient and the Professional, including but not limited to the nature of the Condition being monitored and the preferences of the patient and Professional. Alternatively, the monitoring schedule may be set by the Subject/patient or Professional. Alternatively, the eye-monitoring service may be configured to opportunistically monitor the Subject/patient's eyes when the Subject/patient is using his or her smartphone for other purposes.

h. In step 508, the eye-monitoring service captures images and video of the Subject/patient's eyes. If an eye-monitoring schedule has been set, the eye-monitoring service preferably notifies the Subject/patient when it is time to perform an eye image or video capture. The notification may be provided, without limitation, by smartphone, text message, email, or push notification. The Subject/patient then activates the mobile app of the eye-monitoring service and is prompted to capture images and videos of his or her eyes. Alternatively, if the eye-monitoring service has been configured to opportunistically monitor the Subject/patient's eyes, images and video of the Subject/patient's eyes are captured while the Subject/patient is using his or her smartphone for other purposes.

i. In step 509, the captured images and video are uploaded to a server computer running the server-side application (or "back-end") of the eye-monitoring service. The images and video are tagged with the user's identity, the date and time the images and/or video were captured, and other metadata as appropriate. The images and video are encrypted during transmission and storage to ensure the privacy of the Subject/patient's data. The images are video stored in a database within the server that is designed for efficiently storing, querying, and retrieving high-resolution images and video.

j. In step 510, the server application of the eye-monitoring service retrieves previously stored data concerning the Subject/patient, including but not limited to the Subject/patient's medical history, previously captured eye images and videos, and the purpose for which the Subject/patient is being monitored. This data provides the "context" in which the server application will analyze the Subject/patient's newly captured images and videos.

k. In step 511, the server application evaluates the quality of the captured images and videos to ensure that the images and videos are suitable for analysis. For example, the server application processes the images and videos to detect whether they are too light or too dark and whether position and distance of the eye relative to the camera is appropriate. The threshold for acceptable quality may be determined at least in part by various parameters, such as the disease or Condition for which the Subject/patient is at risk. For example, some conditions may require higher resolution images. If the images and videos were captured according to a schedule, the Subject/patient may be immediately notified whether the images and videos are acceptable or not acceptable. If the images and/or videos are not acceptable, the Subject/patient is prompted to perform the image and video capture again. If the images and videos were captured opportunistically, the images and videos that are not amenable to analysis may simply be discarded.

l. In step 512, the server application derives information from the images and videos. Without limitation, the server application may derive measurements and information relating to the physical dimensions of different parts of the eye, the color of the eye, and/or the movement of the eye. The server application may also compare the images and videos and/or derived measurements and information to previously captured images and videos of the eyes of the same Subject/patient, a known healthy person, or a person known to be affected by a particular Condition or disease. For example, the server application may compute the change in the color of the Subject/patient's eye since the last image or video was captured or compute the difference in color between the Subject/patient's eye and an eye known to be healthy.

m. In step 513, the server application applies machine learning and data analysis techniques known in the art to estimate the likelihood that a health condition or disease is present and the severity of the disease or Condition. The health analysis is configurable in multiple ways by the Subject/patient, Professional, and/or a system administrator. For example, the server application may be configured to analyze the Subject/patient's health with respect to only a specified Condition for which the Subject/patient has a known elevated risk, or the server application may be configured to analyze the Subject/patient's health with regard to a broader set of diseases and conditions. Similarly, the server application may be configured to estimate whether the severity of an existing Condition has increased or decreased or the server application may be configured to only note the presence of a Condition without regard to severity.

n. In step 514, the server application determines whether the health analysis should result in any further action by the eye-monitoring service. The most common action to be taken by the eye-monitoring service is to notify the Subject/patient and/or service provider. The conditions under which a notification is delivered to the Subject/patient and/or service provider is also configurable. For example, the server application may be configured to provide a notification when a new Condition is detected, when an existing Condition is no longer detected, or when the severity of a Condition has changed. Since the health analysis generally produces probabilistic estimates, the server application is also configurable with respect to the confidence thresholds required for a notification to be sent. For example, the Professional may elect to only receive notifications when the health analysis is virtually certain that a Condition has arisen, when there is even a small chance that a Condition has arisen, or anything in between.

o. In step 515, if a notification to the Subject/patient and/or Professional is generated due to a potential health change in the Subject/patient, the Subject/patient and/or Professional may elect to request a video conference with each other using the web-based or app-based interface of the eye-monitoring service. If both parties agree to participate in a video conference, which may be scheduled for some future time, the eye-monitoring service establishes an audio and video link between the two. The audio and video link enables the Professional to gather more information about the Subject/patient's symptoms, including non-eye related symptoms, if any, and conduct further visual inspection of the Subject/patient. Alternatively, the eye-monitoring service may facilitate some other form of communication between the Subject/patient and Professional, such as an audio or text-based chat. The Professional may then determine whether the Subject/patient requires further medical attention. For example, the Professional may elect to schedule an in-person appointment for the Subject/patient or obtain laboratory testing for the Subject/patient.

Some additional information about the embodiments follow:

1. A way to record and transmit "usable" two-dimensional and optionally three dimensional color pictures and videos of the Subjects Eye(s) via a remote connection for one or more of the purposes of the invention.

In embodiments, the "Subjects" who receive the Eye evaluation and/or treatment can include:
1. Living conscious human beings.
2. Living unconscious human beings (e.g., on a football field, in an ambulance, or in surgery).
3. Dead human beings (e.g., in a hospital, or in a police or coroner examination).
4. Living conscious animals (e.g., animal "pets" such as dogs, cats, horses etc., and "livestock" such as cows, steers, pigs, chickens, sheep, and fish on fish farms, etc.).
5. Living unconscious animals (e.g., unresponsive but alive pets or livestock, animals in surgery, etc.).
6. Dead animals (e.g., in a pet hospital, on a livestock farm, in a zoo, in a fish farm, etc.).

In embodiments, "Eye(s)" includes the eye itself and parts of the eye, including the eyelids and eyelashes of the Subjects:
 (i) the sclera (the normally white-colored part of the eye surrounding the black-colored center portion of the eye),
 (ii) the pupil (the black-colored center portion of the eye which determines and dynamically controls the amount of light that is let into the inner eye),
 (iii) the iris (the colored part of the eye that surrounds the pupil),
 (iv) the retina (the light-sensitive tissue lining in the back of an eye where light rays are focused through the cornea, pupil and lens),
 (v) the cornea (the transparent front part of the eye, which covers and lies directly in front of the iris and pupil, and allows light to enter the eye),
 (vi) the lens (the nearly transparent biconvex structure suspended behind the iris of the eye, the sole function of which is to focus light rays onto the retina, which changing its shape, changes the focal distance of the eye),
 (v) the Eye(s)' eyelid(s) (including without limitation their color and/or shape, with their position open, partially closed and/or closed, including eyeball movement beneath closed eyelids),
 (vii) the eye lashes;
 (viii) the eyelid blinks and the eyelid blink rates; and
 (ix) the position of the eyes vis-à-vis each other.

Note: The Eye(s) of the Subject are either in a fixed static state and/or in a dynamic state over a fixed period of time (e.g., the fixed period being the time selected interval period during which a number of pictures or the video recording of the Eye(s) and Eye(s) movements is made).

"Eye(s)" also means eye movements, including without limitation blinking.

2. Embodiments describe a new way to examine (or have examined) the Eye(s) (or portions thereof) of Subjects by human beings and/or artificial intelligence software or any kind of machine language software, for the proposed Applications of the invention, in real-time, near real-time, or delayed time.

a. Enabling a Subject-user (or the owner of a Subject-user if the Subject is an animal) to through various potential input means (which is part of the invention and will be described herein) obtain a real-time, near real-time, and/or delayed time diagnostic and/or inquisitive examination of the Eye(s) of the Subject, either using or not using the Subject's prior reference Eye(s) examination (using the invention or not), from the location of Subject's home, or from another "remote" location, such as, for example, without limitation, a local pharmacy, school, college, government facility, physician's office, eye-professional's office, or hospital (for the Subject without a version of the Eye(s) video input device portion of the invention, or to use a potentially higher quality version of the Eye(s) video input device portion of the invention than the version of the device owned or leased by or in the possession of the Subject).

b. Enabling a third-party non-professional (including, without limitation, caregivers of the Subject, parents of minor children who are the Subject, nurses, and paraprofessionals such as ambulance personnel, police or police detectives, etc.) to obtain a real-time, near real-time, and/or delayed time diagnostic and/or inquisitive examination the Eye(s) of the Subject from the Subject's home or from the location of the third-party non-professional, wherever that might be).

c. Enabling a third-party professional (including, without limitation, ophthalmologists, optometrists, medical doctors, psychiatrists, therapists, psychology professors, etc.) to obtain a real-time, near real-time, and/or delayed time diagnostic and/or inquisitive examination the Eye(s) of the Subject.

d. Enabling game participants in games of truth/veracity to obtain a real-time, near real-time, and/or delayed time diagnostic and/or inquisitive examination the Eye(s) of the Subject.

e. Enabling "teachers/instructors/trainers/physical therapists" and/or Subject-users (humans or animals) to measure Subject-users cognitive load—i.e., the mental difficulty of a task—when performing certain tasks (such as, for example, taking the SAT test, learning to fly a military jet aircraft, or taking a police truth/veracity test).

In another embodiment, an "invention device" is used or worn by a Subject-user which has both output ability, defined according to the embodiments described herein, and also has an input ability according to the various "inputs" described in and as part of the invention. This embodiment can have both audio input and output functionality (as described in and as part of the invention), together with:

(a) an optional additional camera or cameras (either directly tethered to the "invention device" or wireless, powered by batteries or through a power main or through the power of the "invention device") recording the general overall physical environment of the Subject-user in which the testing/instruction/commanding is taking place, whereby the tester/instructor/commander would not need to be at the same physical location as the Subject-user to see and measure all or portions of the physical environment results/responses of the Subject-user (in the Subject-user's environment) to the test/instruction/commands given (as opposed to only the Subject-user's eye data results/responses, as described in the invention).

Hence, with the optional camera or cameras the tester/instructor/commander could remotely in real time, near-real time, or delayed time measure and evaluate the overall physical movement of the Subject-user in the context of the Subject-user's environment. For certain types of evaluation of the Subject-user, real-time evaluation remotely could be very important in order that a corrective test/instruction/command could be provided to the Subject-user in real time to either obtain more data immediately or to potentially obtain a better result/response from the Subject-user for the task at hand.

The combined data could lead to better and quicker evaluation of the Subject-user and assist in a positive manner in the improvement by the Subject-user in the tasks being evaluated.

Examples, without limitation, of the potential usefulness of this embodiment could be:

1. Subject-users being evaluated for neurological conditions, including the loss of certain normal body motions, such as, without limitation, walking or other physical movement.
2. Remote physical therapy and exercise; training athletes.
3. Training police officers, first responders, soldiers, astronauts, and others in high-stress situations.
4. Training dogs (e.g., pets, seeing eye dogs, police dogs, military dogs), horses, and other animals (e.g., without limitation, dolphins, such as in underwater surveillance) in performing certain tasks.

f. Enabling the Eye(s) of a Subject to be examined, or enabling the Subject to have his, her or its Eye(s) examined, whereby a number of combinations and permutations of indications of:

(i) Potential health issues (both Eye(s) health issues per se as well as other health issues for which the Eye(s) may be indicators. Please note that Eye(s) can harbor signs of various chronic diseases and neurological conditions (in addition to Eye(s) diseases per se) which a trained human eye doctor can spot, and based on this invention expert machine learning software and deep learning software can and will spot, enabling the Subject to seek a potential further examination and treatment;

(ii) Cognitive overload—measuring (i) the mental difficulty of a task for a Subject, and then the Subject either solving or giving up on the task over a period of time (and/or comparing the lessened cognitive overload over time, comparing one session to another, as learning occurs), (ii) the truth/veracity in a Subject responding to a question or questions, given it typically involves a significantly greater amount of cognitive load when one is untruthful, (iii) the amount of visual, audio, or touch stimulus generated by certain things (i.e., by the Subject seeing and/or hearing and/or feeling (a haptic stimulus) something that the Subject really likes or does not like and the involuntary response therefrom), and (iv) potential drug use of the Subject (i.e., is the Subject currently under the influence of alcohol or legal or illegal drugs);

(iii) New biometric identifiers and measurements for identification of the Subject for miscellaneous purposes.

The data can be reviewed and analyzed concurrently, in either real-time, near real time (real time other than processing and/or network delays), or delayed-time, thereby saving the Subject time, effort, and potentially "thought" (i.e., the effort by the Subject to think about and/or remember to have his or her Eye(s) examined or measured for any of the purposes of the invention) and allowing for an efficient comprehensive examination of the Subject's Eye(s), and the potential creation, with the appropriate permission of the Subject (or for a Subject who is an animal, the Subject's owner) of an Eye(s) database for:

(i) Use as a future reference with respect to the Subject; and/or (ii) Use for Eye(s) research for humanity and animals in general, including without limitation:

(a) Building and growing new and existing "deep learning" AI systems for better evaluation and/or diagnosis of eye health and potential related body health issues and understanding of cognitive overload (to use it be better and/or less expensively measure the veracity and mental accomplishment of the Subject, and other matters involving the cognitive overload of the Subject);

(b) Building expert software to diagnosis and better understand individual issues related to Eye(s) as they exist in standalone portions of the Eye(s) and in various combinations and permutations with other areas of the Eye(s) and body using "Big Data" and machine learning software and deep learning software, in ways presently known to those skilled in the art, to tease out new correlations that can in the future be used for better health prognosis.

Traditional eye examinations for humans means the human whose eye(s) are to be examined must arrange for an appointment and travel to the location of a Professional who conducts a frequently expensive and time-consuming face-to-face/in-person eye tests. Traditional Eye(s) examinations of Eye(s) for animals means bringing the animal a distance to a veterinarian, or having the veterinarian travel a distance to the location of the animal, to examine the Eye(s) of the animal face-to face/in-person. The invention allows for most of the traditional Eye(s) examination tests for humans and/or animals to be conducted remotely, at-a-distance, in real-time, near real-time or delayed time.

3. The real-time, near real-time, and/or delayed time examination of the Eye(s) of Subjects depicted in:
   a. Real-time third-party images or moving visual depictions of Subjects (as in, e.g., a "live" TV transmission); and/or
   b. Recorded and time-delayed third-party images or moving visual depictions of Subjects in, for example, an analog or digital visual format (as in, e.g., an old film newsreel), in the positives or negatives of photographs, films, and in videos, computer hard drives, DVDs, Blu-Ray disks, or other means of past, present, or future video storage, in a fixed static state and/or dynamic state over a fixed period of time (the "Once-or-More-Removed Eye(s) Exam"); and
4. The ability for a Subject who is a living conscious human, from home or "at-a-distance" (e.g., from a local pharmacy, school, or physician's office, etc., with a high-end version of the "input" portion of the invention, to have a near-replication of a traditional in-person (with a human professional) routine Eye(s) examination, performed on the other end by:
   (i) a human professional, with the output portion of the invention; and/or
   (ii) a "machine" and/or computer with machine vision software, etc.,
including without limitation, an assessment of:
(a) Eye(s) muscle movement,
(b) Visual acuity (how clearly you see),
(c) Refractive error (how light waves pass through the cornea and lens of the eye),
(d) Visual field (how much you can see on either side moving your eyes), of you while not
(e) Color vision,
(f) The physical health of your eyes and the surrounding structures, including lashes and eyelids (and related color, change of color, and movement),
(g) The health of the retina, and
(h) Risk of glaucoma.

By the way, the purpose of the real-time, near real-time, and/or delayed time, and or Once-or-More-Removed Eye Examination (in real-time or delayed) (together, the "Eye(s) Exam") is in part as follows:

1. To attempt to widely broaden access to Eye(s) care by Subjects having the ability to measure or attempt to measure, through a review of the fixed static state and/or dynamic state of the Eye(s) of the Subjects over a fixed period of time, for:
   (i) research purposes (including building a database of comparative data of Eye(s));
   (ii) health diagnostic purposes (the identification of potential or actual health problems), including without limitation follow-up examinations of Subjects following treatment of the Eye(s) of the Subject;
   (iii) prescriptive purposes (the fixing of certain problems, such as prescribing eyeglasses or contact lenses); and
   (iv) general prudent periodic health check-up purposes; and
   (v) the health of and changes over time in various parts of the Eye(s) and other related aspects of the health (insofar as the Eye(s) reveal another disorder with the non-Eye(s) portion of the physical body, or an allergy (new or existing), or with a behavior that affects health (such as the usage of certain prescription or illegal drugs) of the Subjects whose Eye(s) are being examined through such an examination of the Eye(s).

For example, but without limitation, in humans:
a. The Sclera
   (i) If bloody eye(s)/white-of-the-eye (sclera) has red spots, it may indicate high blood pressure or a clotting disorder.
   (ii) If pink eye/white-of-the-eye (sclera) is pink or light-red it could indicate conjunctivitis (an eye infection).
   (iii) Yellow eye(s)/white-of-the-eye (sclera) is yellow could indicate liver diseases such as jaundice, hepatitis and cirrhosis
b. The Pupil
   (i) If the pupil size is different (i.e., different size pupils and droopy eyelids) it could indicate Horner's syndrome (a nervous system disorder), neck aneurysms (blood-filled bulge in blood vessel) and/or tumors.
   (ii) Abnormalities of pupillary response or anisocoria (pupil size asymmetry) have been associated with neurological deterioration and secondary brain injury and are correlated with poor neurological outcomes.
   (iii) Abnormalities of pupillary response may indicate a severe or mild concussion.
c. The Iris
   (i) A golden brown or greenish yellow-colored ring on the cornea, surrounding the iris could indicate Wilson's disease (excess copper collects in tissues, may lead to liver disease).
   (ii) A grey or milky-white-colored ring on the cornea, surrounding the iris could indicate high cholesterol and triglycerides, increased heart attack and stroke risk.
d. The Retina. For example, if you have tiny blood vessels (capillaries) in the back of your eye leak fluid into and under your retina, your retina swells, which may blur or distort your vision, which is an indication of diabetic retinopathy and that you have diabetes.
e. The Cornea. For example, abrasion of the corneal surface or a corneal ulcer may be an indication of dry eyes.
f. The Lens. For example, a clouding or fogging of the lens may indicate a cataract.
g. Color and Shape of the Eyelids
   (i) If eyelids are droopy it could indicate a potential brain tumor, myasthenia gravis (neuromuscular disorder).
   (ii) If eyelid edges are red and itchy or have increased eye-gunk it could indicate dandruff or acne rosacea.
   (iii) Brown spot(s), or a bump with blood vessels, often on the lower eyelid may indicate a tumor (an abnormal growth which may be cancerous).

(iv) If the eyelids have bumpy yellowish patches, small yellow spots on the eyelid, it could indicate high cholesterol.

h. Position of the Eyes.
(i) Crossed eye(s) where one or both eyes turn inwards could indicate an intraocular tumor, and/or a neurologic disorder.

i. Eyelid Blinks and the Rate of Eyelid Blinking.
(i) Unable to close eye(s) or control tears and often one side of the face is weak and droops could indicate Bell's palsy (facial paralysis due to dysfunctional cranial nerve VII).

j. Miscellaneous.
(i) Vanishing eyebrows, in which the outer part of eyebrows disappear could indicate thyroid disease (underactive thyroid).

For example, but without limitation, in animals:

a. Cats
(i) Uveitis. If the eye is cloudy and the iris is red, it could be an indication of inflammation inside the eye (uveitis), which can be treated.
(ii) Corneal Ulcer. If a cat is squinting or its eyes are tearing excessively, there is a possibility of a corneal ulcer (or ulcerative keratitis). Symptoms include red, painful eye, watery eye, squinting, sensitivity to light, eye may remain closed, eye discharge, film over eye.
(iii) Iris Melanosis. Brown "freckles" or patches of pigment on the iris, usually in middle-aged to older cats, could be an indication of iris melanosis. Iris melanosis typically does not cause any problems, but severe cases may result in dysfunction of the iris and sometimes glaucoma (increased eye pressure).
(iv) Glaucoma. Red, cloudy, weepy, and in severe cases, visibly enlarged eyes of a cat could be an indication of glaucoma. Cats can lose their vision and possibly even their eyes if they do not receive timely treatment with medications to lower eye pressure. If an underlying cause to the glaucoma can be identified and successfully treated, the glaucoma should resolve as well.
(v) Cataracts. If the pupils (the normally black center to the eye, vertical in a cat) have a white, grey, or milky appearance, it could be an indication of cataracts. Cataract surgery is available for cats when their vision is severely compromised.
(vi) Iris Melanoma. A new patch of dark pigment on a cat's iris could be an indication of iris melanoma, a potentially serious type of cancer.

b. Dogs
(i) Distichia or Ectopic Cilia. If a dog has squinting, tearing or corneal scratches, the dog may have abnormal eyelashes that are small hairs that grow along the eyelid in the wrong direction (distichia or ectopic cilia) and are causing irritation. The abnormal eyelashes are seen with high magnification, and the condition can be treated. This condition is genetic and usually affects young dogs. Distichia or ectopic cilia in dogs can be treated.
(ii) Cataracts. If a dog has opacities or white areas or white spots in the eye lens (which is normally crystal clear), or if the lens has gone completely white, it could be an indication of cataracts. Cataracts in dogs cause a dog to have blurred vision, decreased vision, or even go blind. They also can cause other eye problems like inflammation inside the eye or glaucoma. In dogs, genetics or diabetes causes cataracts. Dog cataracts can be treated, and cataract surgery is available for dogs when their vision is severely compromised.
(iii) Eye Stye. The upper and lower eyelids are equally susceptible to infection. The inflammation in the glands at the eyelid base gives rise to a stye or a group of styes that can become extremely painful for your dog. The dog stye is highly contagious basically because of the causative agent, the bacterium, *Staphylococcus aureus*.

Styes and cysts are often mistaken for each other, but you can tell a stye from a cyst because the stye will typically have an eyelash hair protruding from the middle of the abscess. Styes usually drain naturally, but the process can be sped up with proper eye treatments.

The dog stye is highly contagious basically because of the causative agent, the bacterium, *Staphylococcus aureus*.

Read more at: https://wagwalking.com/wellness/can-dogs-get-styes-in-their-eyes (iv) Cherry Eye. Dogs have three eyelids—two that are readily visible and an extra one, called the third eyelid, that normally hides from view below the inner corner of the eye. The third eyelid is home to a tear producing gland. Normally, this gland is also invisible, but some dogs have a congenital weakness of the ligaments that hold it in place. When these ligaments fail, the gland pops out of its normal location and looks a bit like a "cherry" stuck at the inner corner of the eye. Because this condition often has a genetic basis, both eyes are usually affected over time. To treat cherry eye, a veterinarian will perform a simple surgery to attach the gland back in a more normal position.

10. Conclusion.

Who among us can track all the potential diseases and conditions of the eyes, body, and/or mind mentioned in the ANNEXES referenced herein? Who among us seeks eye care as often as we should, and does not wait until something truly negative happens before we act? Who among us can detect what is often an asymptomatic disease or condition that could be uncovered early by an eye examination? Who among us has the time, much less the financial resources (even with eye insurance), to have his or her eyes examined and monitored as frequently, periodically, accurately, and as hassle-free as the invention is able to do?

Just as some cars can notify the driver of potential issues with respect to the car without the driver needing to think, in a similar way and in certain modes the invention—once set—can notify the Subject/user of potential concerns with respect to the Subject/user's eyes, body, and/or mental health issues without the Subject/user needing to think.

Functionality/Utility of the Invention/how it Works.

An embodiment uses a portable and/or mobile wireless, and comparatively inexpensive system with a novel method of conducting various types of Eye(s) examinations of Subjects remotely from-a-distance in either real-time, near real-time, or delayed time. The Eye(s) examinations can be conducted at a distance by (i) eye professions, or (i) computers in the cloud using both proprietary and/or open source software, mated with AI deep learning software (with a view to over time replacing a number of the functions of current eye professionals, by making the Eye(s) examination process better, faster, cheaper, and more accurate by removing some of its current subjectivity).

The embodiments use:

1. The "Input-Output Device".
   a. A portable or mobile wireless, portable audio and video transmitting and audio and video receiving "device" (the "Input-Output Device") with a (A) wireless transceiver, (B) potential color display (the "Display"), (C) camera or webcam with the ability to take color digital photos and digital streaming video (collectively, the "Camera"), (D) an optional augmented reality scanner to allow for quasi-3 dimensional photos and videos to be taken, recorded and transmitted, and (E) an optional 3-dimensional camera or multiple cameras to allow for 3 dimensional photos and videos of Eye(s) to be taken, recorded and transmitted. Such an Input-Output Device, includes, without limitation:
  i. Any device with the functionality described above.
  ii. A smartphone, with the functionality described above.
  iii. A pad computer, such as an iPad or an Android-based pad computer, with the functionality described above.
  iv. A laptop computer, with the functionality described above.
  v. A desktop computer, with the functionality described above.
  vi. A thin client, with the functionality described above.
  vii. A zero client with the functionality described above.
2. The Chamber. A device (hereinafter the "Chamber"), similar to a periscope, in which the Subject looks though one end of the Chamber (for the human, with or without glasses or contacts, depending on the nature of the Eye(s) exam), with the Input-Output Device Display and its Camera and display screen being "affixed" and facing inward to the other end of the Chamber. When the Subject looks through the Chamber, magnifying mirrors or non-distorting magnifying lens(es) in the Chamber magnify the Subject's Eye(s) and the Subject sees the lit color display screen of the Input-Output Device and its Camera.
  a. The Chamber performs several important purposes:
    i. It keeps the Subject at a fixed focal length from the Camera of the Input Output Device, and helps hold the Camera and color display screen steady as the Subject looks towards them.
    ii. Through the Chamber's internal mirrors and/or lens(es), the Chamber enlarges the Subject's Eye(s) so the Camera is able to better capture the static and dynamic image of a larger eye and eyelid, etc.
In an alternative embodiment, a macro lens is added on the Camera to better capture the image of a much larger eye and eyelid than would otherwise be the case.
    iii. The Chamber keeps control over the level of light for the Eye(s) exam, so each exam session is an "apples-to-apples" comparison, and so various tests on the Subject's Eye(s) can be performed using light in various ways.
      (a) The level of light entering the Chamber can be controlled by a "dimmer knob or slide" to increase, decrease, strobe, or turn off, etc., the internal light inside the Chamber. Alternatively, and perhaps preferably, the light in the Chamber can be controlled at a distance by the person or software on the host end of the system.
      (b) The brightness of the Input Output Device video display can be altered by the Subject-user or someone near the Subject-user or from the host side.
      (c) The Chamber can potentially be lengthened or shortened in different embodiments.
      (d) The Chamber contains mirrors to enlarge the Eye(s) of the human or animal looking into the Chamber so the Camera of the Input-Out Device sees much larger Eye(s) than would otherwise be the case.
      (e) An AUGMENTED REALITY SCANNER
      (f) An extra camera or 3D camera to take 3D video
      (g) The Chamber has a light inside of it that can be turned on and off and can increase or decrease the brightness of the light (the "Scope Light"), which can be directly controlled by the User [or indirectly controlled by professional at a distance]. Alternative: Control over the Input-Output Device can be provided to the professional at a distance through the means of software known to experts skilled in the art (e.g., such as LOGMEIN), and the professional can take control of the session.
  1. User launches the app in the Input-Output Device (the App) and affixes the Chamber to the Input-Output Device.
  2. The App allows User by voice or the professional to operate the Input-Output Device.

Another embodiment uses a head-up display or heads-up display, also known as a HUD as the display part in any of the embodiments described herein. An HUD is conventionally formed of a transparent display that presents data without requiring users to look away from their usual viewpoints. Although HUDs were initially developed for military aviation, HUDs are now used in commercial aircraft, automobiles, and other (mostly professional) applications.

Primary Components of a Typical HUD. A typical HUD contains three primary components: a projector unit, a combiner, and a video generation computer.

The projection unit in a typical HUD is an optical collimator setup: a convex lens or concave mirror with a cathode ray tube, light emitting diode display, or liquid crystal display at its focus. This setup produces an image where the light is collimated, i.e. the focal point is perceived to be at infinity.

The combiner is typically an angled flat piece of glass (a beam splitter) located directly in front of the viewer, that redirects the projected image from projector in such a way as to see the field of view and the projected infinity image at the same time. Combiners may have special coatings that reflect the monochromatic light projected onto it from the projector unit while allowing all other wavelengths of light to pass through. In some optical layouts combiners may also have a curved surface to refocus the image from the projector.

The computer provides the interface between the HUD (i.e. the projection unit) and the systems/data to be displayed and generates the imagery and symbology to be displayed by the projection unit.

Types. Other than fixed mounted HUD, there are also head-mounted displays (HMDs). Including helmet-mounted displays (both abbreviated HMD), forms of HUD that features a display element that moves with the orientation of the user's head.

Generations. HUDs are split into four generations reflecting the technology used to generate the images.

First Generation-Use a CRT to generate an image on a phosphor screen, having the disadvantage of the phosphor screen coating degrading over time. The majority of HUDs in operation today are of this type.

Second Generation-Use a solid state light source, for example LED, which is modulated by an LCD screen to display an image. These systems do not fade or require the high voltages of first generation systems. These systems are on commercial aircraft.

Third Generation-Use optical waveguides to produce images directly in the combiner rather than use a projection system.

Fourth Generation-Use a scanning laser to display images and even video imagery on a clear transparent medium.

Newer micro-display imaging technologies have been introduced, including liquid crystal display (LCD), liquid crystal on silicon (LCoS), digital micro-mirrors (DMD), and organic light-emitting diode (OLED).

In 2012 Pioneer Corporation introduced a HUD navigation system that replaces the driver side sun visor and visually overlays animations of conditions ahead; a form of augmented reality (AR). Developed by Pioneer Corporation, AR-HUD became the first aftermarket automotive Head-Up Display to use a direct-to-eye laser beam scanning method, also known as virtual retinal display (VRD). AR-HUD's core technology involves a miniature laser beam scanning display developed by Micro Vision, Inc.

In recent years, it has been argued that conventional HUDs will be replaced by holographic AR technologies, such as the ones developed by WayRay that use holographic optical elements (HOE). The HOE allows for a wider field of view while reducing the size of the device and making the solution customizable for any car model. Mercedes Benz introduced an Augmented Reality based Head Up Display while Faurecia invested in an eye gaze and finger controlled head up display.

A prototype HUD has also been developed that displays information on the inside of a swimmer's goggles or a scuba diver's mask. HUD systems that project information directly onto the wearer's retina with a low-powered laser (virtual retinal display) have also been developed.

Quoting from https://en.wikipedia.org/wiki/Head-up_display#cite_note-38]

Holographic Optical Element. A holographic optical element (HOE) is an optical element (such as a lens, filter, beam splitter, or diffraction grating) that is produced using holographic imaging processes or principles. Dichromated gelatin and photoresists are among the holographic recording materials used in forming holographic optical elements.

One use of a holographic optical element is in thin-profile combiner lenses for optical head-mounted displays. A reflective volume hologram is used to extract progressively a collimated image that was directed via total internal reflection in an optical waveguide. The spectral and angular Bragg selectivity of the reflective volume hologram makes it particularly well-suited for a combiner using such light sources as RGB LEDs, providing both good see-through quality and good quality of the projected image. This usage has been implemented in smart glasses by Konica Minolta and Sony.

[https://en.wikipedia.org/wiki/Holographic_optical_element]

The invention, in a manner known to those skilled in the art, proposes to use HUDs, HMDs, and/or HOEs, alone or in any combination or permutation together, as a form of output for use by Professionals and potentially by Subjects or their guardians or, in the case of animals, owners as part of the display.

Automated Analyzer. An automated analyzer is a medical laboratory instrument designed to measure different chemicals and other characteristics in a number of biological samples quickly, with minimal human assistance. These measured properties of blood and other fluids may be useful in the diagnosis of disease. There are many types of automated analyzers, and of note, like the instant invention, they require "minimal human assistance".

Embodiments of the invention describe herein a type of "automated analyzer".

The AutoAnalyzer is an early example of an automated chemistry analyzer using a special flow technique named "continuous flow analysis (CFA)", invented in 1957 by Leonard Skeggs, PhD and first made by the Technicon Corporation. The first applications were for clinical (medical) analysis. The AutoAnalyzer profoundly changed the character of the chemical testing laboratory by allowing significant increases in the numbers of samples that could be processed. Samples used in the analyzers include, but are not limited to, blood, serum, plasma, urine, cerebrospinal fluid, and other fluids from within the body. The design based on separating a continuously flowing stream with air bubbles largely reduced slow, clumsy, and error-prone manual methods of analysis. The types of tests include enzyme levels (such as many of the liver function tests), ion levels (e.g. sodium and potassium, and other tell-tale chemicals (such as glucose, serum albumin, or creatinine).

The automation of laboratory testing does not remove the need for human expertise (results must still be evaluated by medical technologists and other qualified clinical laboratory professionals), but it does ease concerns about error reduction, staffing concerns, and safety, and also, as earlier noted, "allowing significant increases in the numbers of samples that could be processed". The concept of better, faster, cheaper, and more objective comes to mind with respect to both an automated analyzer and the invention, each extending and improving health care and health care outcomes.

As with the automation of laboratory testing, the invention seeks to "ease concerns about error reduction" through the invention's software objectivity, while also, as noted for the AutoAnalyzer, "allowing significant increases in the numbers of samples that could be processed" (which with the invention translates to better, faster and cheaper treatment of Subjects).

[https://en.wikipedia.org/wiki/Automated_analyser]

It is the inventor's view that automated analyzer data for a subject can be added, combined with and correlated with eye data for a Subject (as obtained and processed by the invention) in a number of ways known to those skilled in the art (including the use of relevant "if-then" and/or AI software), to obtain a relative quick and speedy analysis of if there exist meaningful and useful statistical correlations.

(17) Body Temperature Data—Obtaining human or animal body temperature data requires first choosing the body part from which to measure it (for example, without limitation, a rectal measurement, oral measurement, axillary [armpit] measurement, eardrum measurement, or forehead measurement). There are various types of thermometers used to take body temperature, with the type of thermometer used a function of the body part from which temperature is being measured. The body temperature measured is always dependent on where the measurement is taken. [See generally https://www.microlife.com/magazine/fever/how-to-measure-body-temperature-correctly].

1. Human Body Temperature. Body temperature is one of one's vital signs, and it is an important indicator of one's health. Taking a person's temperature is typically an initial part of a full clinical examination. Normal human body-temperature (normothermia, euthermia) is the typical temperature range found in humans. The normal human body temperature range is typically stated as 36.5-37.5° C.(97.7-99.5° F.). Human body temperature varies. It depends on sex, age, time of day, exertion level, health status (such as illness and menstruation), what part of the body the measurement is taken at, state of consciousness (waking, sleeping, sedated), and emotions. No person always has exactly the same temperature at every moment of the day. Body temperature is kept in normal range by thermoregulation, in which adjustment of temperature is triggered by the central nervous system. A temperature setpoint is the level at which the body attempts to maintain its temperature. When the setpoint is raised, the result is a fever. Fever, or pyrexia, happens when the body temperature rises above normal. For humans, generally speaking any body temperature above 98.6°F represents a fever episode. Still, there can be four types: (i) a low fever happens when the body temperature does not exceed 100.4°F, (ii) a moderate fever happens when the temperature ranges between 100.4°F and 102.2°F, (iii) the body temperature of high fever is above 102.2° F., and (iv) there is hyperpyrexia when the temperature is equal to or greater than 104°F. Most fevers are caused by infectious disease. Persistent low-grade or high-grade fevers could signal that something else is going on in your body. A number of medical conditions, including hyperthyroidism and other endocrine disorders, can heighten the body's core temperature. Hypothyroidism, or an underactive thyroid, can also slow down metabolism, which can lead to a drop in body temperature. The body temperature also changes when a person is hungry, sleepy, sick, or cold. [See generally https://en.wikipedia.org/wiki/Human_body_temperature]. [See generally https://health.clevelandclinic.org/body-temperature-what-is-and-isnt-normal/#:~:text=Temperature %20is %20one %20of %20your %20vital %20signs %2 C %20and,temperature %20at %20a %20comfortable %20level %2C %20Dr.%20Ford %20says.]. [See generally https://steptohealth.com/the-relationship-between-body-temperature-and-fever/].

2. Non-Human/Animal Body Temperatures. This normal body temperature is different in different types of animals.

a. Warm-Blooded Animals. Warm-blooded animals, which are mostly mammals and birds, need to maintain a relatively constant body temperature, within a small range (just as the human body, which is a mammalian body), in order for the systems to work properly. [See generally https://vikaspedia.in/agriculture/livestock/general-management-practices-of-livestock/body-temperature]. The body temperatures of mammals range from around 97° to over 103° Fahrenheit. For example, normal body temperature for dogs and cats is 101 to 102.5 degrees Fahrenheit (38.3 to 39.2 degrees Celsius). [See generally https://vcahospitals.com/know-your-pet/taking-your-pets-temperature]. Normal body temperature for horses can range between 98 and 100 degrees. Some horses naturally run hotter than others, but individual horses tend to be fairly consistent day-to-day (which is why it is helpful to get a baseline for one's horse's temperature when he or she is healthy). "An elevated body temperature, commonly called a "fever," can be an early indication of viral or bacterial infection." [See generally https://equusmagazine.com/horse-care/horse-fever-worry #: ~: text=Normal %20body %20temperature %20for %20horses %20can %20ran ge %20between,for %20your %20horse % E2%80%99s %20temperature %20when %2 Ohe %20is %20healthy.]. [See generally https://www.karinabrez.com/blog/2017/12/26/what-is-the-normal-body-temperature-of-a-horse]. Birds have average temperatures of around 105° Fahrenheit. [See generally https://www.goldennumber.net/body-temperatures/].

b. Cold-Blooded Animals. Cold-blooded animals, which include most reptiles, amphibians, fish, and insects, do not maintain a constant body temperature. They get their heat from the outside environment, so their body temperature fluctuates, based on external temperatures. [See https://www.acs.org/content/acs/en/education/resources/highschool/chemmatters/past-issues/archive-2013-2014/animal-survival-in-extreme-temperatures.html]. [See also https://www-.worldatlas.com/articles/warm-blooded-and-cold-blooded-animals-what-is-the-difference.html]. Fish are ectotherms or poikilotherms, both terms that describe animals that have a body temperature that is dependent on the environmental temperature. Such animals are commonly, but incorrectly, called "cold-blooded". Each species of fish has its own minimum and maximum temperature range, and the animal's health is likely to be affected at temperatures outside that range. [See generally https://fishdoc.co.uk/water-temperatures-and-fish-health/].

Determining body temperature of healthy a calf, cow and buffalo, bull, goat, and/or sheep, for example, helps to understand if the animal is affected by diseases or is healthy. If the animal gets affected by any diseases then its body temperature changes frequently. Although there are some other reasons for which temperature can change frequently, the main reason of changing temperature of the animal is: (i) the body temperature of the healthy animal become high in the morning and get reduced at evening, (ii) during mating time temperature increases highly, (iii) the body temperature gets increased at the end of gestation, (iv) the animal working hard for long time, (v) the body temperature get increased after consuming food, and (vi) the body temperature of the animal get reduced suddenly after drinking water. [See generally https://www.roysfarm.com/body-temperature-of-healthy-animal/].

It is the inventor's view that adding, time synchronizing, and comparing and cross-referencing (in a manner and with techniques known to those skilled in the art, and as described in the invention) a Subject's body temperature data together with a Subject's eye data (as captured by and processed as described in the invention), can potentially lead to new discoveries as well as improved health benefits for both humans and animals alike as described in the invention.

An embodiment defines using a Subject's body temperature data, as captured and processed as described above, and time synchronizing and comparing and cross-referencing that body termperature data with the eye data monitoring and analysis, as described in this document, as part of this invention ("eyes data-plus")."

The previous description of the disclosed exemplary embodiments is provided to enable any person skilled in the art to make or use the present invention. Various modifications to these exemplary embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A system for analyzing information, comprising:
a computer, receiving eye data from a user;
wherein the eye data includes information about all of a sclera of the eye, which is a normally white-colored part of the eye surrounding the black-colored center portion of the eye, information about a pupil of the eye, which is a black-colored center portion of the eye, an iris of the eye, which is a colored part of the eye that surrounds the pupil, and a retina of the eye, which is the light-sensitive tissue lining in the back of an eye where light rays are focused through the cornea, pupil and lens,
wherein the computer includes a smartphone which includes a camera, and the eye data is received by using the camera for analyzing eyes of the user who is looking at the phone,
the computer processing the eye data to compare the eye data with information indicative of physical diseases; and
the computer using the comparing to determine a physical disease in the user based on the eye data;
wherein the system also includes a network connection, and the computer also includes a remote computer remote from the smartphone, the remote computer receiving the eye data from the smartphone, analyzing the data, and sending results to the smartphone.

2. The system as in claim 1, wherein the eye data includes information about at least one eyelid of the eye, including its color and shape.

3. The system as in claim 1, wherein the eye data includes information about movement of the eye.

4. The system as in claim 3, wherein the eye data includes the eyelid blinks and the eyelid blink rates.

5. The system as in claim 1, wherein the eye data is received at preselected intervals and for preset selected durations.

6. The system as in claim 1, wherein the processor uses machine learning software, and compares the eye data to each of:
(i) prior eye data of the user,
(ii) eyes-data of other users contextually similar to the user, and
(iii) eye data of "healthy eyes",
and determines said physical disease based on said comparing.

7. The system as in claim 1, wherein the physical disease is a blood disease.

8. The system as in claim 1, wherein the physical disease is an organ disease.

9. The system as in claim 8, wherein the physical disease is a liver disease.

10. A computer system for remotely analyzing information, comprising:
a computer, receiving eye data from a user, the eye data being an image or video, the computer obtaining metadata associated within the image or video, including a format, resolution, creation time, patient name and ID, and storing the image or video along with a record including the metadata in a database;
wherein the eye data includes information about all of a sclera of the eye, which is the normally white-colored part of the eye surrounding the black-colored center portion of the eye, information about a pupil of the eye, which is a black-colored center portion of the eye, an iris of the eye, which is a colored part of the eye that surrounds the pupil, and a retina of the eye, which is the light-sensitive tissue lining in the back of an eye where light rays are focused through the cornea, pupil and lens,
the computer processing the eye data to compare the eye data with past eye data of the same patient, with eye data of a known healthy patient, and with eye data of a known diseased patient, and using the comparing to determine a specific organ disease or blood disease in the user based on the eye data.

11. The computer system as in claim 10, wherein the computer includes a smartphone which includes a camera, and the eye data is received by using the camera for analyzing eyes of the user who is looking at the smartphone, and where the results are sent to the smartphone.

12. The computer system as in claim 10, wherein the eye data includes computed measurements of the eye.

13. The computer system as in claim 10, wherein the computed measurements of the eye include all of computed measurement of at least one of a size and shape of the eye, eyelid, iris, pupil, and retina.

14. The computer system as in claim 10, wherein the computer uses machine learning techniques to quantify a risk that a patient has a particular condition based on the eye data, which includes an image or video of the patient's eye.

15. The computer system as in claim 14, wherein the computer uses the eye data to classify patients as high risk or low risk for a particular condition.

16. The computer system as in claim 15 wherein, if the eye-monitoring service collects images of a patient's eyes and the subsequently the patient is diagnosed with a particular physical disease, this finding is used by the eye-monitoring service as a data point for training the supervised machine learning algorithm.

* * * * *